US006660267B1

(12) United States Patent
Carroll

(10) Patent No.: US 6,660,267 B1
(45) Date of Patent: Dec. 9, 2003

(54) PREVENTION AND TREATMENT OF SEPSIS

(75) Inventor: Sean B. Carroll, Cottage Grove, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 08/304,602

(22) Filed: Sep. 12, 1994

Related U.S. Application Data

(63) Continuation of application No. 07/995,388, filed on Dec. 21, 1992, now abandoned.

(51) Int. Cl.[7] ...................... A61K 39/395; A61K 39/38; C07K 16/00; C12P 21/08

(52) U.S. Cl. ................................ 424/181.1; 424/179.1; 424/180.1; 424/184.1; 424/282.1; 530/319; 530/320; 530/390.1; 530/391.7

(58) Field of Search ........................... 424/181.1, 282.1; 530/319, 320, 390.1, 391.7, 812

(56) References Cited

U.S. PATENT DOCUMENTS

| 4,703,039 A | * | 10/1987 | Hawinger et al. ............ 514/21 |
| 4,867,973 A | * | 9/1989 | Goers et al. ................ 530/388 |
| 4,918,163 A | | 4/1990 | Young et al. ................ 530/387 |

FOREIGN PATENT DOCUMENTS

| EP | 428486 | 11/1990 |
| FR | 2342740 | 3/1977 |

OTHER PUBLICATIONS

Drabicu et al (1992) Clinical Research, vol. 40. No. 2, p. 287 Abstract.*
Cross et al., Inf. Immun., 1993, 61(7):2741, Minireview, Choice; Sepsis.*
Jawltz et al., Review of Medical Microbiology, 1984, pp. 122–135 & 142.*
Biotechnology Newswatch, Oct. 4, 1993, Another sepsis . . . receptor.*
The Merck Manual, 15th Edition, 1987, pp. 48–50 and 222–225.*
The Merck Manual, 16th Edition, 1992, pp. 70–74 and 2025–2031.*
G.W. Machiedo et al., Surg. Gyn. & Ob., 152:757–759 (1981).
D.D. Morris et al., Am. J. Vet. Res., 47:2554–2565 (1986).
A.M. Hoffman et al., J. Vet. Int. Med., 6:89–95 (1992).
S.M. Wolff, New Eng. J. Med., 324: 486–488 (1991).
D.C. Morrison, Rev. Infect. Dis., 5 (Supp 4) :S733–S747 (1983).
R.C. Bone, Ann. Intern. Med., 115:457–469 (1991).
K.J. Tracey et al., Science 234:470–474 (1986).
A. Tewari et al., Lancet 336:712–714 (1990).

Bérdy in Advances in Applied Microbiology, (D. Perlman, ed.), Academic Press, New York, 18:309–406 (1974).
D.G. Maki, Am. J. Med., 70:719–732 (1981).
J.L. Shenep and K.A. Morgan, J. Inf. Dis., 150:380–388 (1984).
D.C. Morrison and D.M. Jacobs, Immunochem., 13:813–818 (1976).
D. Rifkind and J.D. Palmer, J. Bact., 92:815–819 (1966).
D.C. Morrison and D.M. Jacobs, Infect. Immun., 13:298–301 (1976).
M.S. Cooperstock, Antimicrob. Agents Chemother., 6:422–425 (1974).
Physicians' Desk Reference, 47th Ed., pp. 818–819 (1993).
P.E. Hallaway et al., Proc. Natl. Acad. Sci. USA 86:10108–10112 (1989).
M.J. Poznansky and L.G. Cleland in Drug Delivery Systems: Characteristics and Biomedical Applications, (R.L. Juliano, ed.), Oxford University Press, New York, pp. 253–315 (1980).
L. Molteni in Drug Carriers in Biology and Medicine, (G. Gregoriadis, ed.), Academic Press, New York, pp. 107–125 (1979).
C. Larsen, Adv. Drug Delivery Rev., 3:103–154 (1989).
A.D. Virnik et al., Russian Chem. Rev., 44:588–602 (1975).
G. Brownlee et al., Brit. J. Pharmacol., 7:170–188 (1952).
Reynolds et al., in Martindale—The Extra Pharmacopoeia, 28th Ed., The Pharmaceutical Press, London, pp. 512–513 (1982).
W.A. Gibby et al., Invest. Radio., 25:164–172 (1990).
J.J. Corrigan, Jr. and B.M. Bell, J. Lab. Clin. Med., 77:802–810 (1971).
B. Hughes et al., Br. J. Pharmac., 74:701–707 (1981).
J.J. Corrigan, Jr. and J.P. Kiernat, Pediat. Res., 13:48–51 (1979).
G. Ziv and W.D. Schultze, Am J. Vet. Res., 44:1446–1450 (1982).
G. Baldwin et al. J. Infect. Dis., 164:542–549 (1991).
A.H.L. From et al., Infect. Immun., 23:660–664 (1979).
C.J. Ingoldby et al., Am. J. Surgery 147:766–771 (1984).
C.J.H. Ingoldby, Br. J. Surg., 67:565–567 (1980).
J.W. Walterspiel et al., Pediat. Res., 20:237–241 (1986).
A.M. Munster et al., J. Burn Care Rehab., 10:327–330 (1989).
J.D. Baumgartner and M.P. Glauaer, Rev. Infect. Dis., 9:194–205 (1987).
E.J. Ziegler, J. Infect. Dis., 158:286–290 (1988).
W.R. McCabe et al., New Eng. J. Med., 287:261–267 (1972).

(List continued on next page.)

Primary Examiner—Lynette F. Smith
(74) Attorney, Agent, or Firm—Medlen & Carroll, LLP

(57) ABSTRACT

Compositions and methods are described for preventing and treating sepsis in humans and animals. Surgical patients, low birth weight infants, and burn and trauma victims can be treated prophylactically. Methods for treating acute infections are provided with advantages over current therapeutic approaches.

32 Claims, 11 Drawing Sheets

OTHER PUBLICATIONS

A.I. Braude et al., J. Infect. Dis., 136(Supp):S167–S173 (1977).
J.E. Pennington and E. Menkes, J. Infect. Dis., 144:599–603 (1981).
E.J. Ziegler et al., New. Eng. J. Med., 307:1225–1230 (1982).
W.R. McCabe et al., J. Infect. Dis., 158:291–300 (1988).
D.L. Dunn et al., Surgery 96:440–446 (1984).
S.J. Spier et al., Circulatory Shock 28:235–248 (1989).
N.N.H. Teng et al., Proc. Natl. Acad. Sci. USA 82:1790–1794 (1985).
E.J. Ziegler et al., New. Eng. J. Med., 324:429–436 (1991).
R.L. Greenman et al., JAMA 266:1097–1102 (1991).
K.A. Schulman et al., JAMA 266:3466–3471 (1991).
K. Ohlsson et al., Nature 348:550–552 (1990).
S.M. Opal et al., J. Infect. Dis., 161:1148–1152 (1990).
J.–D. Baumgartner et al., Lancet 2:59–63 (1985).
T. Calandra et al., J. Infect. Dis., 158:312–319 (1988).
S. Harkonen et al., Antimicrob. Agents Chemother., 32:710–716 (1988).
C.J. Fisher et al., Clin. Care Med., 18:1311–1315 (1990).
C.H.J. Ford et al., Indian J. Pediatr., 57:29–46 (1990).
H.F. Deutsch in *Methods in Immunology and Immunochemistry*, (C.A. Williams and M.W. Chase, eds.), Academic Press, New York, pp. 315–321 (1967).
E.J. Cohn et al., J. Am. Chem. Soc., 68:459–475 (1946).
G.L. Mandell and M.A. Sande in *Goodman and Gilman's: The Pharmacological Basis of Therapeutics*, 8th Ed., (Gilman, Rall, Nies, and Taylor, eds.), Pergamon Press, New York, pp. 1065–1097 (1990).
M.A. Sande and G.L. Mandell in *Goodman and Gilman's: The Pharmacological Basis of Therapeutics*, 8th Ed., (Gilman, Rall, Nies, and Taylor, eds.), Pergamon Press, New York, pp. 1117–1145 (1990).
A. Fiechter, Trends in Biotech., 10:208–217 (1992).
G.L. Mandell and M.A. Sande in *Goodman and Gilman's: The Pharmacological Basis of Therapeutics*, 8th Ed., (Gilman, Rall, Nies, and Taylor, eds.), Pergamon Press, New York, pp. 1146–1164 (1990).
R.G. Douglas, Jr. in *Goodman and Gilman's: The Pharmacological Basis of Therapeutics*, 8th Ed., (Gilman, Rall, Nies, and Taylor, eds.), Pergamon Press, New York, pp. 1182–1201 (1990).
J.E. Bennett in *Goodman and Gilman's: The Pharmacological Basis of Therapeutics*, 8th Ed., (Gilman, Rall, Nies, and Taylor, eds.), Pergamon Press, New York, pp. 1165–1181 (1990).
T. Nakamura et al., J. Biol. Chem., 263:16709–16713 (1988).
G. Alpert et al., J. Infect. Dis., 165:494–500 (1992).
R.R. Schumann et al., Science 249:1429–1431 (1990).
M.N. Marra et al., J. Immunol., 148:532–537 (1992).
Pierce Chemical Co., (Rockford, IL), General Catalog, pp. E–10–E–39 (1992).
I.S. Snyder and R.G. Finch in *Modern Pharmacology*, 2d Ed., (C.R. Craig and R.E. Stitzel, eds.), Little, Brown and Company, Boston, pp. 631–640 (1986).
J.E. Conte, Jr. and S.L. Barriere, *Manual of Antibiotics and Infectious Disease*, 6th Ed., Lea and Febiger, Philadelphia, pp. 135–152 (1988).
L.E. Hood et al., *Immunology*, 2d Ed., The Benjamin/Cummings Publishing Company, Inc., Menlo Park, pp. 339–340 (1984).
M. Pollack et al., J. Clin. Invest., 72:1874–1881 (1983).
S.H. Zinner and W.R. McCabe, J. Infect. Dis., 133:37–45 (1976).
B.J. Stoll et al., Serodiagnosis and Immunotherapy 1:21–31 (1987).
W. Marget et al., Infection 11:84–86 (1983).
C. Stoll et al., Infection 13:115–119 (1985).
E.S. Caplan and N. Hoyt, Am. J. Med., 70:638–640 (1981).
M. Meek et al., J. Burn Care Rehab., 12:564–568 (1991).
T.J. Zuerlein et al., Clin. Ped., 29:445–447 (1990).
R.L. Nichols in *Decision Making in Surgical Sepsis*, B.C. Decker, Inc., Philiadelphia, pp. 20–21 (1991).
K. Hanasawa et al., Surg. Gyn. & Ob., 168:323–331 (1989).
K. W. Talmadge and C.J. Siebert, J. Chrom., 476:175–185 (1989).
T. Kitagawa et al., J. Assoc. Anal. Chem., (1985).
J.W. Goding, *Monoclonal Antibodies: Principles and Practice*, Academic Press, New York, p. 84 (1986).
S. Barandun et al., Vox Sang., 7:154–174 (1962).
A. Chonn et al., J. Immunol., 146:4234–4241 (1991).
C. Galanos et al., Proc. Natl. Acad. Sci. USA 76:5939–5943 (1979).
A. Traunecker et al., Nature 339:68–70 (1989).

\* cited by examiner

PREVENTION AND TREATMENT OF SEPSIS

This is a Continuation of application Ser. No. 07/995,388 filed on Dec. 21, 1992 now abandoned.

FIELD OF THE INVENTION

The present invention relates to therapeutics for the prevention and treatment of blood-borne and toxin mediated diseases, and in particular the prevention and treatment of sepsis in humans as well as animals.

BACKGROUND OF THE INVENTION

I. Sepsis

Sepsis is a major cause of morbidity and mortality in humans and animals. It is estimated that 400,000–500,000 episodes of sepsis resulted in 100,000–175,000 human deaths in the U.S. alone in 1991 and has become the leading cause of death in intensive care units among patients with non-traumatic illnesses [G. W. Machiedo et al., Surg. Gyn. & Ob., 152:757–759 (1981)]. It is also the leading cause of death in young livestock, affecting 7.5–29% of neonatal calves [D. D. Morris et al., Am. J. Vet. Res., 47:2554–2565 (1986)], and is a common medical problem in neonatal foals [A. M. Hoffman et al., J. Vet. Int. Med., 6:89–95 (1992)]. Despite the major advances of the past several decades in the treatment of serious infections, the incidence and mortality due to sepsis continues to rise [S. M. Wolff, New Eng. J. Med., 324:486–488 (1991)].

Sepsis is a systemic reaction characterized by arterial hypotension, metabolic acidosis, decreased systemic vascular resistance, tachypnea and organ dysfunction. Sepsis can result from septicemia (i.e., organisms in the blood stream), including bacteremia (i.e., bacteria in the blood), as well as toxemia (i.e., toxins in the blood), including endotoxemia (i.e., endotoxin in the blood). Thus, the systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (septic shock). Most patients who enter septic shock die.

There are three major types of sepsis characterized by the type infecting organism. Gram-negative sepsis is the most common type of sepsis and the majority of these infections are caused by *Escherichia coli, Klebsiella pneumoniae* and *Pseudomonas aeruginosa,* and have a case fatality rate of about 35%. Gram-positive pathogens such as the Staphylococci and Streptococci are the other major cause of sepsis, with fungal infections causing a relatively small percentage of cases (with a high incidence of mortality, however). Many of these infections are acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses).

The toxic components of gram-negative bacteria are the best understood. There is a common cell-wall structure known as lipopolysaccharide (LPS) that is widely shared among gram-negative bacteria. The "endotoxin" produced by gram-negative organisms is comprised of three major structures, a lipoprotein, a lipid (lipid A), thought to be responsible for most of the biological properties of endotoxin, and polysaccharide structures unique to each species and distinct strains of bacteria [D. C. Morrison, Rev. Infect. Dis., 5(Supp 4):S733–S747 (1983)]. Research over the past decade or so has demonstrated that purified endotoxin can elicit all of the features of full-blown gram-negative bacteremia. Furthermore, several of the host responses to endotoxin have been identified. Two key mediators of septic shock are tumor necrosis factor (TNF) and interleukin-1 (IL-1) which are released by macrophages and appear to act synergistically in causing a cascade of physiological changes leading to circulation collapse and organ failure [R. C. Bone, Ann. Intern. Med., 115:457–469 (1991)]. Indeed, large doses of TNF [K. J. Tracey et al., Science 234:470–474 (1986)] and/or IL-1 [A. Tewari et al., Lancet 336:712–714 (1990)] can mimic the symptoms and outcome of sepsis.

It is generally thought that the distinct cell wall substances of gram-positive bacteria and fungi trigger a similar cascade of events, although the structures involved are not generally as well studied as gram-negative endotoxin. Many patients with septicemia or suspected of having septicemia exhibit a rapid decline over a 24–48 hour period. Unfortunately, a confirmed diagnosis as to the type of infection requires that microbiological cultures be made, which usually requires several days for plating, growth, and identification. Therefore, therapy must be initiated without any knowledge of the type and species of the pathogen, and with no means of knowing the extent of the infection.

II. Prevention and Treatment

A. Antibiotics

Antibiotics of enormously varying structure [Bérdy in *Advances in Applied Microbiology,* (D. Perlman, ed.), Academic Press, New York, 18:309–406 (1974)] are widely used to prevent and control infections. Nonetheless, up to one half of the patients in whom bacteremia develops in the hospital die [D. G. Maki, Am. J. Med., 70:719–732 (1981)]. The causes for this are many-fold. First, antibiotic resistance is common among most species of bacteria for many antibiotics. Therefore, while physicians commonly prescribe antibiotics for patients at risk, this only aids the selection for antibiotic-resistant organisms. Furthermore, in a hospital setting, the spread of antibiotic-resistant organisms is facilitated by the high density of potentially infected patients and the extent of staff-to-staff and staff-to-patient contact. Second, those antibiotics that are the most economical, safest, and easiest to administer may not have a broad enough spectrum to suppress certain infections. For example, many antibiotics with broader spectrums are not deliverable orally and physicians are reluctant to place patients on intravenous lines due to the enhanced risk of infection. Third, antibiotics can be toxic to varying degrees including causing allergy, untoward interactions with other drugs and direct damage to major organs (e.g., kidneys, liver). Many potent antibiotics are eliminated from routine use due to the probability of adverse reactions at therapeutic doses. Fourth, many antibiotics alter the normal intestinal flora and frequently cause diarrhea and nutritional malabsorption; some may even unleash opportunistic organisms such as *Clostridium difficile* that can cause life-threatening infections of the gastrointestinal tract. Physicians must therefore consider the impact of prophylactic antibiotic use on the development of resistant organisms, on patient health, and on the economics of health care.

While many infections are controlled by antibiotics, gram-negative bacteremia presents some special challenges. It has been shown that treatment of bacteria with antibiotics actually catalyzes endotoxin release from dying cells as their cell walls disintegrate. In experimental *E. coli* sepsis in rabbits, antibiotics cause a 10 to 2,000 fold increase in endotoxin levels despite decreasing levels of bacteremia [J. L. Shenep and K. A. Morgan, J. Inf. Dis., 150:380–388 (1984)]. Thus, once gram-negative bacteremia is established, there is justifiable concern that antibiotic therapy may augment symptoms while mitigating the infection.

Certain antibiotics are known that neutralize the activity of endotoxin. The polymyxin antibiotics, most notably polymyxin B and polymyxin E (also known as colistin) are cyclic polypeptide compounds produced by certain strains of *Bacillus polymyxa*. These antibiotics bind to the lipid A portion of endotoxin [D. C. Morrison and D. M. Jacobs, Immunochem., 13:813–818 (1976)] and neutralize endotoxin activity as measured by lethality tests in animals [D. Rifkind and J. D. Palmer, J. Bact., 92:815–819 (1966)], activation of serum complement [D. C. Morrison and D. M. Jacobs, Infect. Immun., 13:298–301 (1976)], and the Lamellas amebocyte lysate (LAL) assay [M. S. Cooperstock, Antimicrob. Agents Chemother., 6:422–425 (1974)]. Unfortunately, the polymyxins are not absorbed from the GI tract and must be administered parenterally. At the recommended therapeutic dose for systemic infections by *P. aeruginosa* (1–2.5mg/kg body weight/day), there is a significant risk of renal impairment [Physicians' Desk Reference, 47th Ed., pp. 818–819 (1993)]. This is a major concern in patients already suffering from kidney disease. In addition to nephrotoxicity, neurotoxic reactions have been observed, the most severe being respiratory paralysis when given soon after anesthesia and/or muscle relaxants. Polymyxin, in its intravenous form, is only given to hospitalized patients under constant supervision and monitoring of renal function. As such, polymyxins are not used routinely for systemic infections (but they are quite common as components of topical ointments).

Several approaches have been taken to reduce the toxicity of polymyxins. Colistin exhibits a lower systemic toxicity, and when complexed as methanesulfonate salt, the locally severe pain experienced at intramuscular injection sites is diminished. The toxicity of polymyxin B is also reduced by attachment to dextran, a high molecular weight carrier [D. A. Handley, Eur. Patent Appl. Pub. No. 428486]. Conjugation to dextran is often used in an attempt to decrease the toxicity and/or increase the circulating half-lives of drugs [P. E. Hallaway et al., Proc. Natl. Acad. Sci. USA 86:10108–10112 (1989); M. J. Poznansky and L. G. Cleland in *Drug Delivery Systems: Characteristics and Biomedical Applications*, (R. L. Juliano, ed.), Oxford University Press, New York, pp. 253–315 (1980); L. Molteni in *Drug Carriers in Biology and Medicine*, (G. Gregoriadis, ed.), Academic Press, New York, pp. 107–125 (1979); C. Larsen, Adv. Drug Delivery Rev., 3:103–154 (1989); A. D. Virnik et al., Russian Chem. Rev., 44:588–602 (1975); Hager et al., French Patent No. 2,342, 740 (1977)]. Polymyxin has a half-life, for example, of only a few hours [G. Brownlee et al., Brit. J. Pharmacol., 7:170–188 (1952)] while dextran (M. W. 70,000) has a half-life in humans of about a day, depending upon the dose infused [Reynolds et al., in *Martindale—The Extra Pharmacopoeia*, 28th Ed., The Pharmaceutical Press, London, pp. 512–513 (1982); W. A. Gibby et al., Invest. Radio., 25:164–172 (1990)].

Polymyxin B has been investigated as a specific therapy for gram-negative sepsis or endotoxemia over the past 20 years in both animal models and human trials but with mixed results. For example, endotoxin-induced disseminated intravascular coagulation (DIC) was not prevented in rabbits administered polymyxin B fifteen (15) minutes after endotoxin challenge [J. J. Corrigan, Jr. and B. M. Bell, J. Lab. Clin. Med., 77:802–810 (1971)]. In fact, most experimental studies have shown a requirement for premixture of endotoxin and polymyxin B or administration of polymyxin B prior to endotoxin challenge to reduce or abolish the effects of endotoxin [D. Rifkind and J. D. Palmer, J. Bact., 92:815–819 (1966); J. J. Corrigan, Jr. and B. M. Bell, J. Lab. Clin. Med., 77:802–810 (1971); B. Hughes et al., Br. J. Pharmac., 74:701–707 (1981); J. J. Corrigan, Jr. and J. F. Kiernat, Pediat. Res., 13:48–51 (1979); G. Ziv and W. D. Schultze, Am. J. Vet. Res., 44:1446–1450 (1982); G. Baldwin et al. J. Infect. Dis., 164:542–549 (1991)]. Some studies have found little benefit to polymyxin B, even as a pretreatment [A. H. L. From et al., Infect. Immun., 23:660–664 (1979)]. Importantly, clinical studies on endotoxemia in human obstructive jaundice found no benefit to polymyxin B therapy [C. J. Ingoldby et al., Am. J. Surgery 147:766–771 (1984)], consistent with results in animal models [C. J. H. Ingoldby, Br. J. Surg., 67:565–567 (1980)].

Low dose polymyxin B therapy has also been investigated in animals and humans. In the infant rat, subinhibitory doses of polymyxin B, administered 12 hours after infection with live Haemophilus influenzae Type B organisms alone or in combination with a large dose of ampicillin, significantly reduced mortality due to the infection. The theory here is that the polymyxin B neutralizes endotoxin released by organisms killed by other antibiotics. [J. W. Walterspiel et al., Pediat. Res., 20:237–241 (1986).] It should be noted that the design of this experiment differed from the endotoxin challenge experiments, in that live organisms, not free endotoxin were the starting materials for the challenge. In humans, continuous infusion of subtherapeutic doses of polymyxin B (10–50% of normal dosage) was found to reduce endotoxin levels, restore some immune functions, and apparently (i.e., results were not statistically significant) reduce wound infection in burn patients [A. M. Munster et al., J. Burn Care Rehab., 10:327–330 (1989)].

B. Immunization

In addition to antibiotic research and development, the effort to control bacterial infections has focused on the role of host defenses, and in particular, the humoral immune system. The role of active immunization against bacterial components and the utility of passive immunization with antibodies or plasma derived from immunized donors is a highly controversial area. While there is abundant experimental evidence that specific antibodies can protect experimental animals from infections and toxin challenge, the nature and degree of this protection and its relevance to in vivo infection is not clear despite the large volume of literature on the subject [J. D. Baumgartner and M. P. Glauser, Rev. Infect. Dis., 9:194–205 (1987); E. J. Ziegler, J. Infect. Dis., 158:286–290 (1988)]. Disease progression in the critically ill patient, and its prevention, involves a myriad of factors that has complicated the design and interpretation of human clinical trials.

In gram-negative bacteremia and endotoxemia, it was found that the frequency of septic shock was inversely related to the titer of antibodies cross-reactive with shared antigens of bacterial LPS [W. R. McCabe et al., New Eng. J. Med., 287:261–267 (1972)]. Given this correlation, an enormous effort has been expended to develop a means of raising endotoxin antibody titers and/or passively transferring endotoxin antibody from donors to experimental subjects and patients.

Antibodies to endotoxin have two important functions. First, by binding free endotoxini antibodies may block endotoxin activity or remove it from the circulation. Second, immunoglobulin effector functions such as complement fixation and binding to Fc receptors on phagocytes can mediate killing and opsonophagocytosis of bacteria. Thus, endotoxemia, bacteremia, and the onset of sepsis, may be thwarted by such antibodies.

i) Active Immunization

One approach to protecting animals and humans from endotoxin-mediated effects is by immunization with bacteria or LPS. For example, it has been shown that immunization of rabbits with a mutant *E. coli* strain (J5) lacking certain polysaccharide side chains but possessing a widely shared core lipid A structure can protect the animals from challenge with live Pseudomonas bacteria [A. I. Braude et al., J. Infect. Dis., 136(Supp):S167–S173 (1977)]. The J5 vaccine was found to be only weakly protective in a guinea pig model of Pseudomonas pneumonia, whereas a species-specific Pseudomonas LPS was greatly protective [J. E. Pennington and E. Menkes, J. Infect. Dis., 144:599–603 (1981)]. These results suggest that species-specific vaccines could be superior to cross-protective antigens in immunizing hosts against endotoxin. Unfortunately, the vast diversity of LPS antigens makes the former an unlikely prospect.

While active immunization against endotoxin continues to be investigated, there are some important limitations to this approach. First, endotoxin is a weak vaccine, eliciting only a three- to five-fold increase in antibody titers to LPS with virtually no booster response [E. J. Ziegler et al., New. Eng. J. Med., 307:1225–1230 (1982)]. Second, many patients at risk for sepsis are immunocompromised and may not mount and/or sustain a sufficient response to a vaccine. And third, the degree of cross-protection afforded by immunization with one or more core glycolipid antigens is not well understood clinically.

ii) Passive Immunization

In order to overcome some of the limitations inherent to active immunization, various techniques have been used to produce endotoxin-binding antibodies that could be passively transferred to experimental animals or human subjects. A large number of endotoxin antibodies have been prepared by: (i) immunization of animals or humans with bacteria or LPS or derivatives thereof and collection of immune serum or plasma or (ii) production of monoclonal murine or human antibodies and collection and purification of these antibodies by established methods.

The two major antibody types elicited by either procedure are IgM and IgG antibodies. These antibodies differ in important aspects of their structure and effector functions as well as their titer in normal and hyperimmune plasma. Most studies suggest that IgM antibodies, by virtue of their greater avidity are more effective than IgG antibodies at protecting animals [W. R. McCabe et al., J. Infect. Dis., 158:291–300 (1988)] and humans [Id.; E. J. Ziegler et al., New. Eng. J. Med., 307:1225–1230 (1982)] from gram-negative bacteremia or endotoxin challenge. However, it should be noted that numerous IgG preparations from immunized animal donors have been developed and demonstrated to have some protective effect in experimental studies [D. L. Dunn et al., Surgery 96:440–446 (1984); S. J. Spier et al., Circulatory Shock 28:235–248 (1989)]. The advantage to IgG preparations is that IgG titers may increase in response to repeated immunization whereas IgM titers are relatively constant. No matter what the immunization course, however, the total amount of bacterially-reactive or endotoxin-reactive antibodies in hyperimmune plasma or serum is only a small fraction of total antibody and is highly variable from donor to donor.

In order to develop more consistent preparations of therapeutic antibodies, numerous LPS-reactive monoclonal antibodies have been developed to both shared and unique epitopes. Since gram-negative sepsis can be caused by a number of species, emphasis has been placed on widely cross-reactive antibodies as potential therapeutics. Two IgM monoclonal antibodies have received the most study. A human-derived antibody now known as Centoxin-HA-IA [N. N. H. Teng et al., Proc. Natl. Acad. Sci. USA 82:1790–1794 (1985)] and a mouse-derived antibody now known as XOMEN-E5 [Young and Alam, U.S. Pat. No. 4,918,163] have been tested in both animals and humans. The animal data suggest that both antibodies are capable of binding endotoxin, neutralizing its biological activity, and suppressing gram-negative bacteremia. Unfortunately, the human clinical studies have not yielded clear benefits [E. J. Ziegler et al., New. Eng. J. Med., 324:429–436 (1991); R. L. Greenman et al., JAMA 266:1097–1102 (1991)] despite the optimism of the authors and sponsors of these trials. The U.S. Food and Drug Administration has refused to approve either antibody for the treatment of sepsis based upon the extended clinical trials performed to date.

It should be noted that each antibody was tested in humans after the onset of symptoms of sepsis and when the type of organism was uncertain. It is widely believed that anti-endotoxin antibody treatment administered after sepsis is established may yield little benefit because these antibodies cannot reverse the cascade of inflammatory mediators triggered by endotoxin such as TNF and IL-1. In addition, the high cost of each antibody (Centoxin HA-1A is priced at $3700 per 100 mg dose) makes physicians hesitant to use a product where no clear benefit has been demonstrated [K. A. Schulman et al., JAMA 266:3466–3471 (1991)]. Of course, these endotoxin antibodies only target gram-negative sepsis, no equivalent antibodies exist for the array of gram-positive organisms and fungi.

III. Inhibiting Cytokines Released During Sepsis

With new knowledge regarding the effects of endotoxin on host inflammatory responses, other therapies are being targeted towards blockage of interleukin-1 and tumor necrosis factor functions. For example, an interleukin-1 receptor antagonist has been identified that occupies the same receptor site as IL-1 but mediates no biological effect. Blockage of the IL-1 receptor with this molecule can reduce mortality from endotoxin shock [K. Ohlsson et al., Nature 348:550–552 (1990)]. The IL-1 receptor antagonist appears to be well-tolerated but the required dosage is extremely large, over 100 mg of recombinant protein per kg of body weight is infused over a period of hours to days. For human therapy, the 8–10 grams of recombinant protein anticipated to be required is likely to be extremely costly (several thousand dollars).

TNF therapies target the removal of this mediator from the circulation. Monoclonal antibodies have been found to offer some protection in experimental animals [S. M. Opal et al., J. Infect. Dis., 161:1148–1152 (1990)] but studies in human patients with sepsis have not been concluded. Once again, these antibodies are likely to be expensive therapeutic agents to be administered only when signs of sepsis are present.

IV. Prophylaxis

Since the treatment of ongoing septicemia presents so many challenges, there have been several attempts at prevention. These attempts have provided mixed results. One promising study utilized hyperimmune plasma against core glycolipid in surgical patients at high risk of infection. While antibody prophylaxis did not lower the infection rate, it did reduce the severity of gram-negative infections and improved the survival of such patients [J.-D. Baumgartner et al., Lancet 2:59–63 (1985)]. Numerous studies using intravenous immunoglobulin, collected from large numbers of normal donors and containing a wide range of antibodies, have given mixed results [J. D. Baumgartner and M. P. Glauser, Rev. Infect. Dis., 9:194–205 (1987)]. The primary limitations to these studies would appear to be the variable and relatively low potency of pooled immunoglobulin preparations that were used [T. Calandra et al., J. Infect. Dis., 158:312–319 (1988)].

Monoclonal antibodies have also been made. While these preparations should possess greater potency, their high cost, immunogenicity [S. Harkonen et al., Antimicrob. Agents Chemother., 32:710–716 (1988)] and unusually short circulating half-lives (less than 24 hr) [S. Harkonen et al., Antimicrob. Agents Chemother., 32:710–716 (1988); C. J. Fisher et al., Clin. Care Med., 18:1311–1315 (1990)] make them unattractive candidates for prophylaxis.

Clearly, there is a great need for agents capable of preventing and treating sepsis. These agents must be capable of neutralizing endotoxin action in gram-negative sepsis as well as controlling and reducing bacteremia. It would be desirable if such agents could be administered prophylactically in a cost-effective fashion. Furthermore, approaches are needed to combat all forms of sepsis, not just gram-negative cases.

SUMMARY OF THE INVENTION

The present invention relates to therapeutics for the prevention and treatment of blood-borne and toxin mediated diseases, and in particular the prevention and treatment of sepsis in humans as well as animals. In one embodiment, the present invention relates to compositions and methods for preventing sepsis in high-risk patients (e.g., surgical patients, low birth weight infants, and burn and trauma victims). In another embodiment, the present invention contemplates treatment of humans and animals having symptoms of a systemic septic reaction.

In accordance with the present invention, a member from the class of compounds broadly described as antibody-antibiotic conjugates or "antibodiotics" is employed for intravenous, intramuscular, intrathecal or topical administration. Antibiotics are comprised of antibody (e.g., IgG, IgM, IgA) to which an antibiotic is covalently attached to make an antibody-antibiotic conjugate. Preferably, the antibody is non-specific IgG. By non-specific, it is meant that no single specificity within the antibody population or pool is dominant. Thus, it is to be contrasted with the use of antigen-specific antibodies.

In one embodiment, the present invention contemplates an antibiotic-antibody conjugate, comprising antibiotic covalently bound to non-specific immunoglobulin. It is preferred that the immunoglobulin is IgG having an Fc region and is capable of binding to phagocytic cells via the Fc region.

In one embodiment, the conjugate is capable of binding to bacteria via the antibiotic. The conjugate may be bacteriostatic, bactericidal or both.

However, the antibiotics contemplated are not limited to antibacterial agents; antifungal agents and antiviral agents are also contemplated. Where antibacterial antibiotics are used, agents effective against both gram-positive and gram-negative organisms are contemplated.

The present invention contemplates conjugates capable of binding lipopolysaccharide on gram negative bacteria as well as conjugates capable of binding free endotoxin and neutralizing free endotoxin.

Preferred antibiotics include polymyxins, and specifically polymyxin B. Polymyxin is a known endotoxin-binding compound capable of binding free endotoxin.

The present invention also contemplates a therapeutic preparation, comprising antibiotic covalently bound to non-specific immunoglobulin, wherein the preparation is bactericidal for both gram-positive and gram-negative organisms. In one embodiment of the therapeutic preparation, the antibiotic is selected from the group comprising cephalosporins and penicillins. In another embodiment, the therapeutic preparation further comprises: (i) a first conjugate consisting of a first antibiotic covalently bound to non-specific immunoglobulin; and (ii) a second conjugate consisting of a second antibiotic covalently bound to non-specific immunoglobulin (e.g., where the first antibiotic is polymyxin and the second antibiotic is bacitracin). In still another embodiment of the therapeutic preparation, two different antibiotics are covalently bound to the same immunoglobulin molecule, one capable of binding to gram-positive organisms and the other capable of binding to gram-negative organisms.

The present invention contemplates a method of treatment, comprising: (a) providing a mammal for treatment; (b) providing a therapeutic preparation, comprising an endotoxin-binding compound covalently bound to protein; and (c) administering the preparation to the mammal (e.g., intravenous). The endotoxin-binding compound may be polymyxin and the protein is preferably non-specific immunoglobulin such as IgG.

The treatment with the antibodiotic is expected to have many of the effects of the antibiotic alone—however, without the toxicity and short half-life typically associated with these agents. Furthermore, these conjugates are expected to possess the opsonizing function of immunoglobulin which may facilitate clearance of both the toxin and organism.

DESCRIPTION OF THE DRAWINGS

FIG. 3 outlines an alternative method by which new antibiotics can be screened for use as compounds for conjugation with immunoglobulins.

DESCRIPTION OF THE INVENTION

Figure 1A:
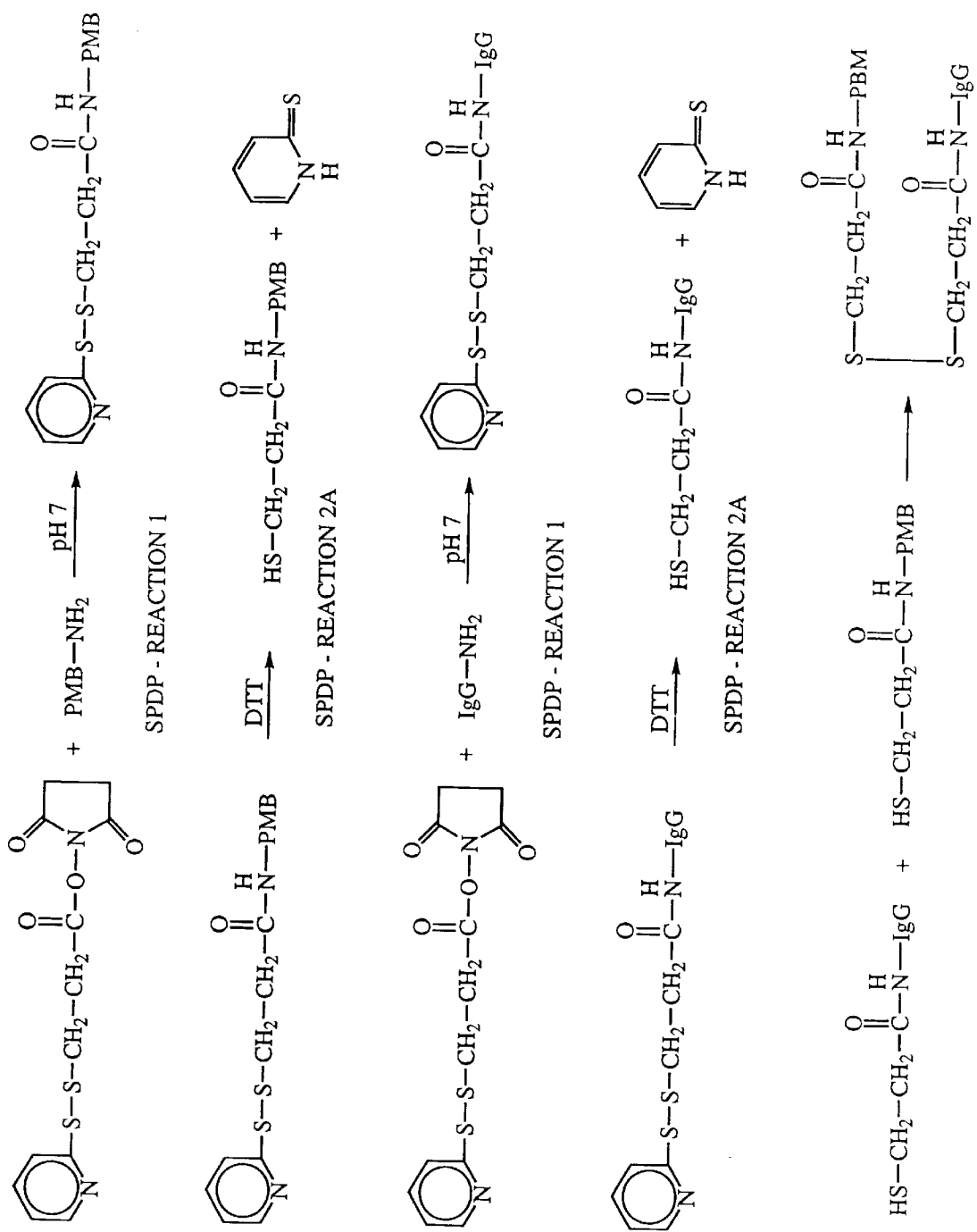
FIG. 1A schematically shows the design of an antibodiotic of the present invention.
Figure 1B:
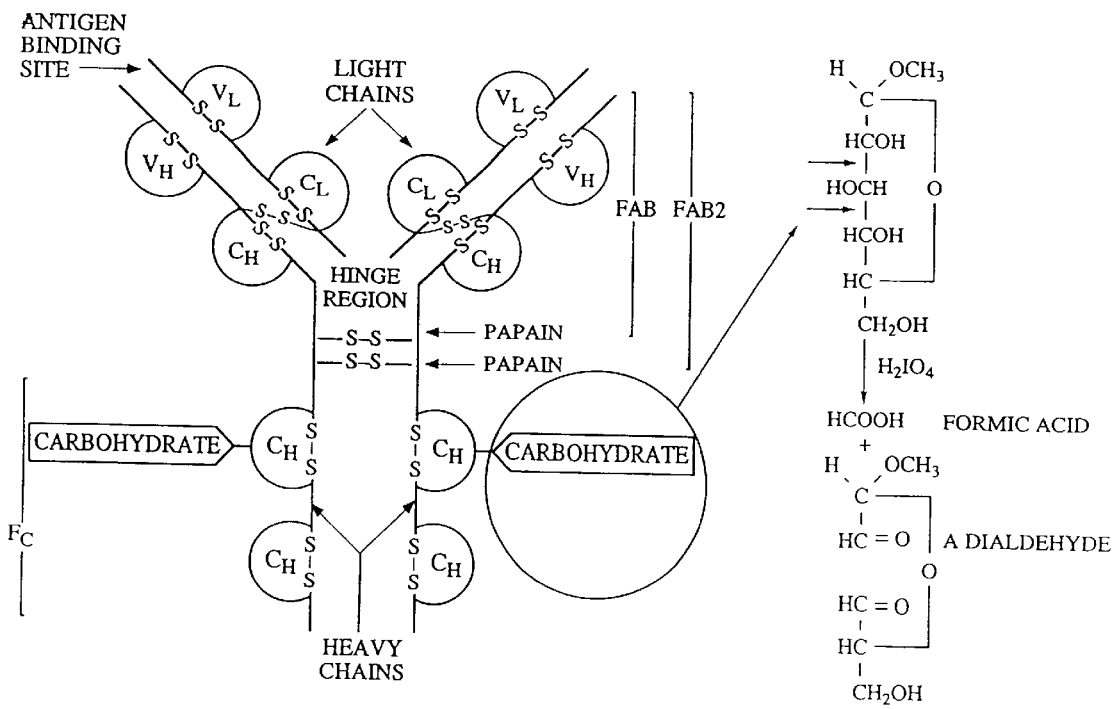
FIG. 1B schematically shows the design of another antibodiotic of the present invention.
Figure 1B:
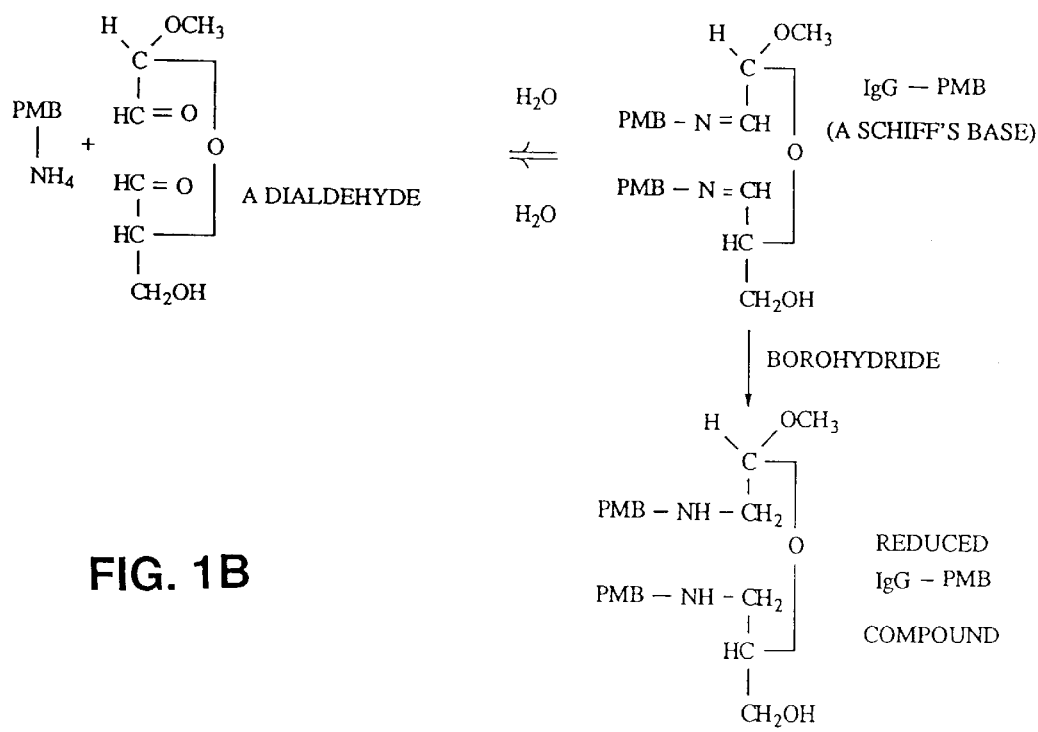

The present invention relates to therapeutics for the prevention and treatment of blood-borne and toxin mediated diseases, and in particular the prevention and treatment of sepsis in humans as well as animals. In accordance with the present invention, soluble antibody-antibiotic conjugates or "antibodiotics" are administered intravenously, intramuscularly, intrathecally or topically. The conjugate is water-soluble if it has a solubility in water of at least 0.1 mg/ml, and preferably of at least 1.0 mg/ml, when measured at room temperature. The present invention contemplates the use of antibodiotics in a therapeutic preparation for both prophylactic and acute treatment.

While the benefit conveyed by treatment according to the present invention is not dependent on the understanding of the mechanism(s) by which soluble antibody-antibiotic conjugates achieve a therapeutic result, it is believed that, in the case of bacteria, success is accomplished by: (i) binding and opsonization of bacteria; (ii) bacterial killing (direct killing by the conjugate and/or complement mediated); and (iii) neutralization and removal of free bacterial toxins (e.g., gram-negative endotoxin, thereby preventing initiation and/or escalation of the septic reaction).

It is believed that antibodiotics provide a low cost, reasonably effective and needed preventative. Antibodiotics can suppress fungal and viral infection. Furthermore, antibodiotics suppress bacteremia as well as endotoxin-mediated effects. Antibodiotics with long duration of action (e.g., days to weeks are easily administered. Furthermore, since the invention encompasses antibodiotics with reactivity against gram-negative organisms as well as antibodiotics with reactivity to gram-positive organisms, a wider spectrum of protection is expected than any other known approach.

The description of the invention involves: (I) Antibodiotic Design and Characterization; (II) Antibodiotic in vitro and in vivo Efficacy; (III) Antibodiotic Applications; and (IV) Therapeutic Preparations and Combinations. Section III describes the use of antibodiotics for: (A) Prophylactic Use in Humans; (B) Acute Therapy in Humans; and (C) Veterinary Care.

I. Antibodiotic Design and Characterization

A. Antibodies

In designing antibodiotics, all types of antibody (e.g., IgG, IgM, IgA) are contemplated. Nonetheless, there are advantages to using a particular class of antibody. Table 1, for example, compares the characteristics of IgG and IgM. While IgM has the advantage of better opsonization and complement activation, IgG has a longer half-life in vivo and can be raised to higher titers because of the fact that it is the primary antibody of a secondary response to antigen. Consequently, the preferred antibody for conjugation according to the present invention is IgG.

While antigen-specific IgG can be employed (e.g., bacteria-seeking antibodies), antigen-specificity may result in a shorter half-life (arid/or greater cost). Consequently, the preferred antibody is non-specific [contrast C. H. J. Ford et al., Indian J. Pediatr., 57:29–46 (1990)].

For purposes of expense, IgG from donors (i.e., human and animal) rather than cells lines is desirable. In this regard, typically large pools of plasma are used as starting material. Large scale fractionation techniques known in the art include ethanol precipitation and precipitation with high concentrations of salt. [See H. F. Deutsch in *Methods in Immunology and Immunochemistry*, (C. A. Williams and M. W. Chase, eds.), Academic Press, New York, pp. 315–321 (1967).] There is also the somewhat complicated procedure where the immunoglobulin is isolated from Cohn Effluent III by disfiltration and ultrafiltration. [See E. J. Cohn et al., J. Am. Chem Soc., 68:459–475 (1946).]

This latter procedure is used to make a commercially available human IgG preparation called Gamimune® N (Miles, Inc., West Haven, Conn.). Of course, each individual donor used to make the products must be tested and found nonreactive for pathogens. In this product, which is intended for intravenous administration, the protein (as a 4.5–5.5% solution) has not been chemically modified other than in the adjustment of the pH of the solution to 4.0–4.5. Isotonicity is achieved by the addition of (9–11%) maltose.

TABLE 1

|  | IgM | IgG |
| --- | --- | --- |
| Structure | pentameric | monomeric |
| C' fixation | +++ | + |
| Opsonophagocytosis | +++ | + |
| Half-life | 5 days | 25 days |
| Biodistribution | slow | fast |
| Secondary response | minimal | large |

Each milliliter (ml) contains approximately 50 mg of protein, of which not less than 98% has the electrophoretic mobility of gamma globulin. Not less than 90% of the gamma globulin is monomer. There are traces of IgA and IgM. The distribution of IgG subclasses is similar to that found in normal serum.

The commercial product displays a broad spectrum of opsonic and neutralizing antibody activities. When administered intravenously, essentially 100% of the infused IgG antibodies are immediately available in the recipient's circulation. The in vivo half-life equals or exceeds the three week half-life reported for IgG in the literature. It is therefore quite acceptable for use in the preparation of antibody-antibiotic conjugates of the present invention.

Of course, the infusion of large amounts of antibody in humans is contraindicated in individuals who are known to have had previous anaphylactic or severe systemic responses to IgG. Care must also be taken to confirm that there is no sensitivity to the trace amounts of other antibody (e.g., IgA).

Before administration of the antibody-antibiotic conjugates of the present invention to humans, it may be good medical practice to have an antibodiotic sensitivity test performed. This can be done by subcutaneously injecting a small amount of the conjugate in the arm of the patient. A salt solution is injected in the other arm as a control. Normally, a positive hypersensitivity test is indicated by no more than formation of a welt on the skin surface with surrounding swelling. Some patients, however, develop anaphylactic shock, i.e., a full hypersensitivity reaction. It is recommended that adrenalin be available for these cases.

The usual dosage of the commercial intravenous immunoglobulin product is 100–200 mg/kg (2–4 ml/kg) of body weight administered approximately once a month by intravenous infusion. The dosage may be given more frequently or increased as high as 400 mg/kg (8 ml/kg) body weight, if the clinical response is inadequate, or the level of IgG achieved in the circulation is felt to be insufficient.

The present invention contemplates a typical dosage for antibodiotics that is much less than that given for the commercial immunoglobulin preparations. This is particularly true where the number of conjugated antibiotic molecules exceeds one (1) per immunoglobulin molecule. The present invention contemplates a conjugate dosage range of 0.1–100 mg/kg, and a preferred range of 1–20 mg/kg. The amount of PMB (assuming 3 molecules per IgG molecule) contained in a dose for this preferred range will be 0.025–0.5 mg/kg.

B. Antibiotics

Thousands of natural, synthetic, and semi-synthetic compounds have been identified that possess anti-bacterial, antifungal, antiviral, or antiparasitic activity. In the design of antibody-antibiotic conjugate, a primary consideration is the mode of action of the antibiotic. Since the conjugates will be much larger molecules than the parent antibiotics, only antibiotics that bind to exposed or secreted components (e.g., toxins) of the bacteria, fungus, virus, or parasite are likely to target the antibody carrier to the pathogen or its products. For example, penicillin antibiotics disrupt bacterial cell wall synthesis and bind to surface-exposed components of certain bacteria whereas aminoglycoside antibiotics commonly bind to ribosome subunits in the cell cytoplasm. The former is a much better candidate for effective antibody-antibiotic conjugates than the latter.

Antibiotics vary greatly in the type and species of organisms upon which they are active. For example, certain antibiotics such as the polymyxins are far more effective against gram-negative bacteria whereas other antibiotics such as vancomycin are effective against some gram-positive bacteria. Some, like the penicillins and cephalosporins, are comparably effective against both types. Other antibiotics, such as amphotericin are primarily antifungal agents whereas amantadine exhibits activity against certain influenza viruses. In designing antibody-antibiotic conjugates for the prevention or treatment of disease one has to consider the spectrum of antibiotic activity desired and select those antibiotics that are active against the target pathogen(s) and, as described above, act primarily on exposed components of the pathogen(s).

Within a family of antibiotics (e.g., penicillins, cephalosporins, polymyxins) there are structural features common to all members. However, there often exists a wide variety of natural and synthetic variations on this common structure that may influence the activity spectrum, pharmacokinetics, or other properties of the antibiotic. In the design of antibody-antibiotic conjugates, these structural differences within an antibiotic family are important from two perspectives. First, the activity spectrum may influence the choice of antibiotic; and, second, the chemical differences between antibiotics will influence the range of cross-linking chemistries available to conjugate the antibiotic. For example, the variable side chain component of penicillin antibiotics is a methyl benzyl group in penicillin G but the variable side chain group is a phenolic group with a primary amine side chain in amoxicillin. The latter antibiotic presents a wider array of potential modes for cross-linking than does penicillin G.

In Table 2, several families of antibiotics are disclosed that possess surface- and/or product-reactive activities against various pathogens. This is just for illustration and by no means is intended to limit the invention to these compounds alone.

A preferred antibiotic of the present invention is polymyxin B (PMB). As noted above, this antibiotic binds to and neutralizes endotoxin. However, when used in vivo PMB is short-lived, and furthermore, at the recommended therapeutic dose for systemic infections, there is a significant risk of nephrotoxicity.

The level of protection achieved by the present invention is best understood when compared with other known approaches (see Table 3). For example, the widely-tested and publicized monoclonal antibody Centoxin-HA-IA is capable of binding endotoxin and neutralizing its biological activity. However, when compared to an IgG-PMB conjugate of the present invention, the monoclonal antibody is costly and suffers from low affinity and short half-life. The latter characteristics may explain why the human clinical studies have not yielded clear benefits.

Others have attempted to reduce the toxicity of polymyxin B by attachment to dextran [D. A. Handley, Eur. Patent Appl. Pub. No. 428486]. However, dextran has a half-life in humans of only about a day. By use of immunoglobulin according to the present invention, a much longer half-life is achieved (see Table 4). Dextran, having no Fc receptor (FcR), also has no known capacity to promote opsonization or activate complement (C').

As noted previously, the present invention also contemplates antibodiotics having reactivity with gram-positive organisms and their toxins. In one embodiment, the present invention contemplates the use of bacitracin conjugated to immunoglobulin.

TABLE 2

Antibiotics That May Be Conjugated To Antibodies

| Type | Examples | Activity | Spectrum |
|---|---|---|---|
| Penicillins[1] | penicillin G, amoxicillin | antibacterial, inhibition of cell wall synthesis | gram-positive and gram-negative |
| Cephalosporins[2] | cefoxitin, ceforanide | antibacterial, inhibition of cell wall synthesis | gram-positive and gram-negative |
| Polymyxin | polymyxin B, colistin | antibacterial binds and inhibits cell wall synthesis | primarily gram-negative |
| Vancomycin[3] | vancomycin, teicoplanin, ristocetin | antibacterial, binds to cell wall precursor, inhibits synthesis | primarily gram-positive |
| Biosurfactants[4] | circulin, EM49, polypeptin, brecistin, cerexin, tridecephin, surfactin | surface-active | bacterial |
| | surfactin, subsporin, mycosubtilisin, bacillomycin | surface-active | fungicidal |

TABLE 2-continued

Antibiotics That May Be Conjugated To Antibodies

| Type | Examples | Activity | Spectrum |
| --- | --- | --- | --- |
| Other Peptide antibiotics[5] | viomycin, capreomycin | not known | antimycobacterial (tuberculostatic) |
| | bacitracin, gramicidin, gramicidin S, tyrocidine | surface-active | antibacterial |
| amantadine[6] | amantadine | blocks ion channel | antiviral, influenza A |
| polyene macrolide[7] | amphotericin | surface activity on membrane sterols | antifungal |
| endotoxin binding proteins[8] | tachyplesin | surface active | bacterial |
| [9] | limulus anti-LPS factor | LPS-binding | antiendotoxin |
| [10] | LPS binding protein (human) | LPS-binding | antiendotoxin |
| [11] | bactericidal permeability increasing protein | LPS-binding | antiendotoxin |

[1]G.L. Mandell and M.A. Sande in Goodman and Gilman's: The Pharmacological Basis of Therapeutics, 8th Ed., (Gilman, Rall, Nies, and Taylor, eds.), Pergamon Press, New York, pp. 1065–1097 (1990).
[2]Id.
[3]M.A. Sande and G.L. Mandell in Goodman and Gilman's: The Pharmacological Basis of Therapeutics, 8th Ed., (Gilman, Rall, Nies, and Taylor, eds.), Pergamon Press, New York, pp. 1117–1145 (1990).
[4]A. Fiechter, Trends in Biotech., 10:208–217 (1992).
[5]G.L. Mandell and M.A. Sande in Goodman and Gilman's: The Pharmacological Basis of Therapeutics, 8th Ed., (Gilman, Rall, Nies, and Taylor, eds.), Pergamon Press, New York, pp. 1146–1164 (1990).
[6]R.G. Douglas in Goodman and Gilman's: The Pharmacological Basis of Therapeutics, 8th Ed., (Gilman, Rall, Nies, and Taylor, eds.), Pergamon Press, New York, pp. 1182–1201 (1990).
[7]J.E. Bennett in Goodman and Gilman's: The Pharmacological Basis of Therapeutics, 8th Ed., (Gilman, Rall, Nies, and Taylor, eds.), Pergamon Press, New York, pp. 1165–1181 (1990)
[8]T. Nakamura et al., J. Biol. Chem., 263:16709–16713 (1988).
[9]G. Alpert et al., J. Infect. Dis., 165:494–500 (1992).
[10]R.R. Schumann et al., Science 249:1429–1431 (1990).
[11]M.N. Marra et al., J. Immunol., 148:532–537 (1992).

TABLE 3

| | CENTOXIN | IgG-PMB |
| --- | --- | --- |
| Dosage | 100 mg | 100–500 mg |
| Raw material cost | $300 | $2–10 |
| Endotoxin affinity | low | high |
| Half-life | short (<24 hr) | long (>20 days) |
| Safety | good | good |

TABLE 4

| | DEXTRAN-PMB | Ig-PMB |
| --- | --- | --- |
| Carrier | Polysaccharide | Protein |
| Conjugation chemistry | Carbonyl, amide | —SH, CHO, $NH_2$ |
| Cross-linkers? | No | Yes |
| Bactericidal | ? | Yes |
| Exp. half-life | ≦24 hr | >20 days |
| Effector for C' | No | Yes |
| FcR | No | Yes |
| Additional reactivities | No | Yes (IVIG) |

Bacitracin is primarily active, against gram-positive organisms including *Streptococcus pneumoniae, Streptococcus pneumoniae,* β*-haemolytic streptococci* and certain strains of *Clostridia*. While it is not intended that the present invention be limited by the mechanisms of action, it is believed that bacitracin exerts its bactericidal action by interfering with cell-wall synthesis.

Like PBM, nephrotoxicity limits the clinical use of free bacitracin in the treatment of systemic infections. However, when conjugated to immunoglobulin according to the present invention, the advantages of bacitracin can be achieved without this side-effect.

C. Conjugates and Cross-linking

Numerous agents have been developed for the cross-linking of biological molecules [Pierce Chemical Co., (Rockford, Ill.), General Catalog, pp. E-10–E-39 (1992)]. In general, these agents possess functional groups that are reactive with the side chains of different amino acids found in proteins or peptides. As summarized in Table 5, various functional groups will react with primary amino groups, carboxyl groups, hydroxyl groups, or thiol groups of proteins or other compounds. In the design of antibody-antibiotic conjugates, the reactive groups of both the antibody and antibiotic must be considered. In general, antibodies have many reactive groups that can be used in direct conjugation schemes (amino acids containing primary amine, carboxyl, hydroxyl, thiol [after reduction]) or modified groups (glycosylated amino acids that can be oxidized to aldehyde, or primary amines that can be made thiol-reactive) for conjugation schemes. Individual antibiotics will not, in general, possess very many different reactive groups and offer fewer choices for conjugation to antibodies. The selection of an antibiotic from a family of related compounds and the selection of a cross-linking scheme must take into consideration the reactive groups on an antibiotic.

A key concern in modifying an antibiotic is the preservation of its ability to bind to the surface or secreted products of a pathogen. The modification of individual reactive groups or excessive modification of more than one reactive group with cross-linking agents, or the steric hindrance created by attachment to a large protein such as immunoglobulin may abolish antibiotic activity. Therefore, before conjugate activity is considered, conditions for preservation of antibiotic activity must be determined by examining the biological activity of the modified or cross-linked antibiotic in simple antimicrobial assays. Preferably, one chooses a cross-linker type and concentration that preserves antibiotic activity.

Different cross-linkers may influence the activity of individual antibiotics and the efficiency with which they are conjugated to antibodies. In the design of antibody-antibiotic conjugates, the discovery of more optimal cross-linkers relies on the empirical analysis of conjugates prepared using varying concentrations of different cross-linkers.

The in vivo safety and efficacy of antibody-antibiotic conjugates will depend upon their activity, toxicity and stability. The selection of the cross-linking agent may also affect these aspects of conjugate performance. For example, in addition to influencing the activity of the conjugate imparted by the antibiotic, the cross-linker employed may affect the properties of the antibody. Effector functions dependent upon the Fc region of the antibody such as opsonization or complement fixation may be influenced by which reactive groups are utilized and their location on the antibody molecule. Furthermore, some cross-linkers may cause adverse reactions by eliciting an immune response to the haptenic groups on the cross-linker. Finally, the in vivo stability of the bonds created by the cross-linking scheme may vary in important ways. Disulfide bonds linking the antibiotic and antibody may not be as stable, for example, as amide bonds created by other cross-linkers. Dissociation between antibody and antibiotic may not be tolerable in cases where long-term prophylaxis is desired.

D. Analogues

The present invention contemplates the use of antibody analogues. Antibody analogues are those compounds which act in an analogous manner to antibodies. In one embodiment, the present invention contemplates fragments of antibodies (e.g., Fc fractions) to make antibody-antibiotic conjugates.

TABLE 5

| Conjugates | |
| --- | --- |
| Functional Groups | Reacts With: |
| Aldehyde | Primary amines |
| Imide | Primary amines |
| Amino | Aldehyde |
| Cyano | Hydroxyl groups |
| Halogen (e.g., Bromine) | Thiol groups |
| Carboxyl groups | Primary amines |
| Activated carboxyl groups (e.g., N-succinimidyl esters of carboxylic acids)* | Primary amines or hydroxyl groups |
| Anhydrides (e.g., succinic anhydride and maleic anhydride) | Primary amines |
| Maleimide derivatives | Thiol groups |

*e.g., N-hydroxyl succinimide ester of N-(-4-carboxycyclo-hexyl methyl) maleimide.

As herein used, the terms "antibody" and "immunoglobulin" are meant to include antibody analogues.

E. New Antibiotics And Conjugates

Antibiotic compounds have been isolated from many different microbial, plant, and animal sources and new promising compounds continue to be discovered. In addition, synthetic derivatives of natural compounds as well as wholly synthetic compounds such as small peptides are also being screened for antibiotic activities in many laboratories. The invention contemplates the design and synthesis of a variety of antibody-antibiotic conjugates utilizing antibiotics from all sources.

Figure 2:
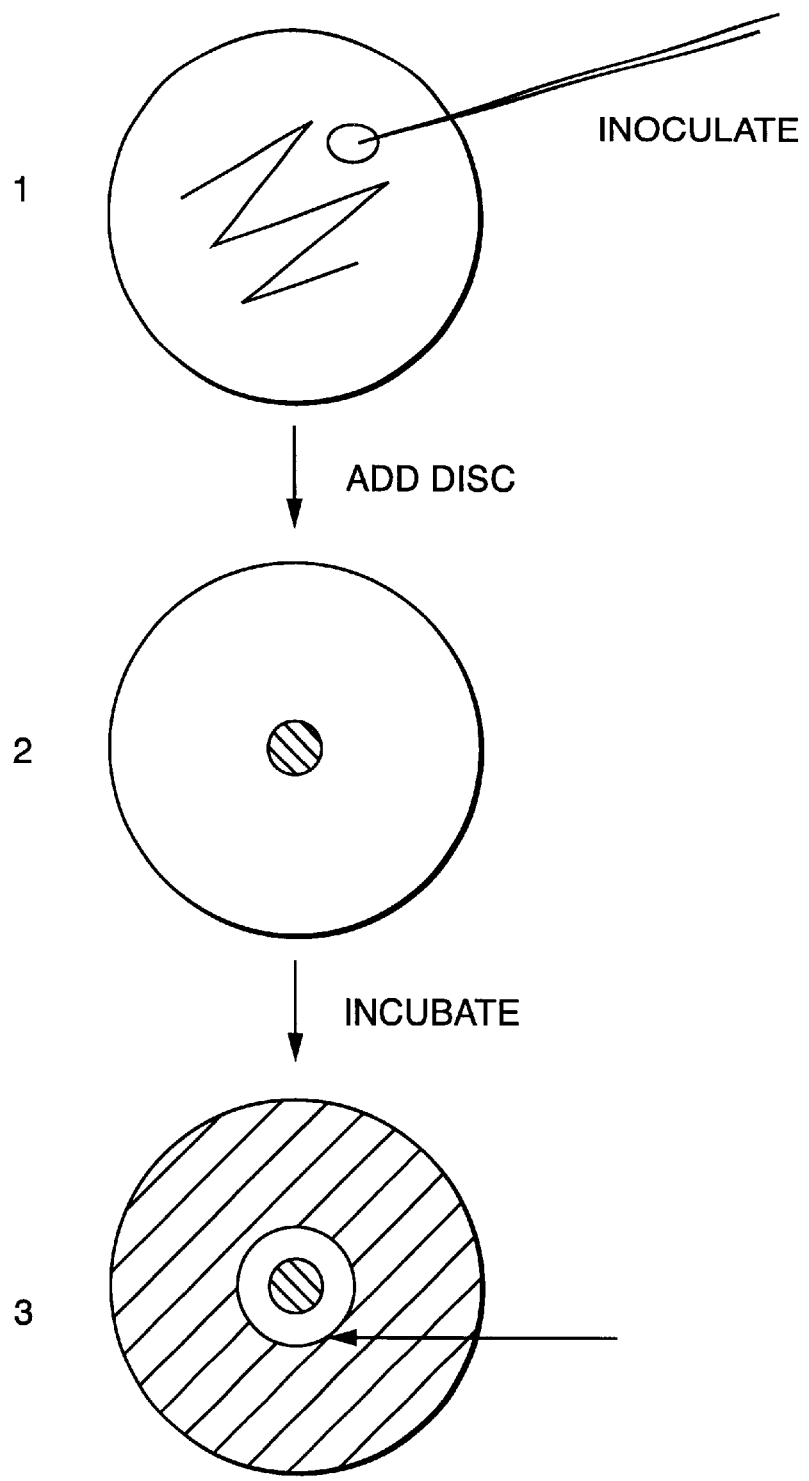
FIG. 2 schematically shows a means of screening modified antibiotics for anti-bacterial activity.
Figure 3A:
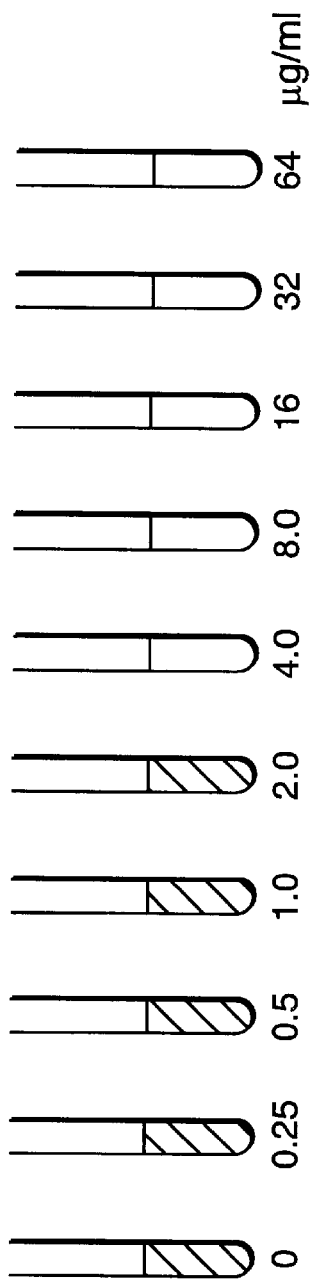
FIG. 3A shows a means by which the minimum concentration for bacterial growth inhibition is established.
Figure 3B:
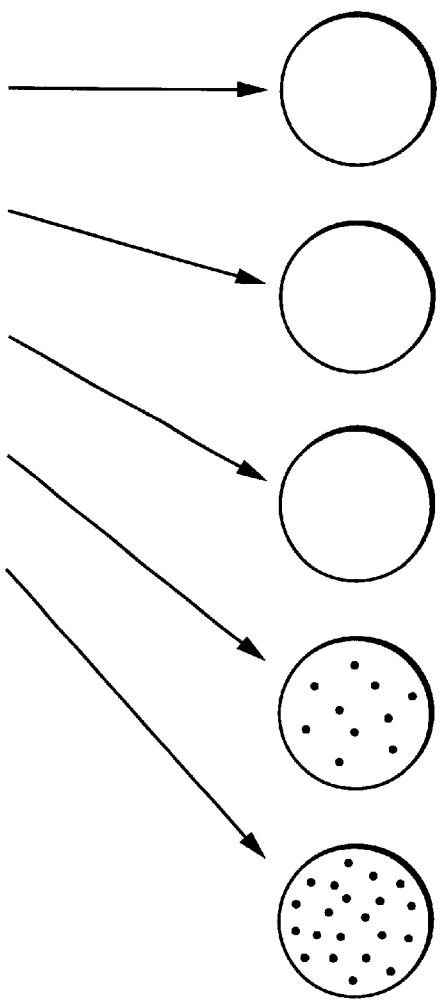
FIG. 3B shows a means by which a new antibiotic can be assessed for bactericidal activity.
Figure 4:
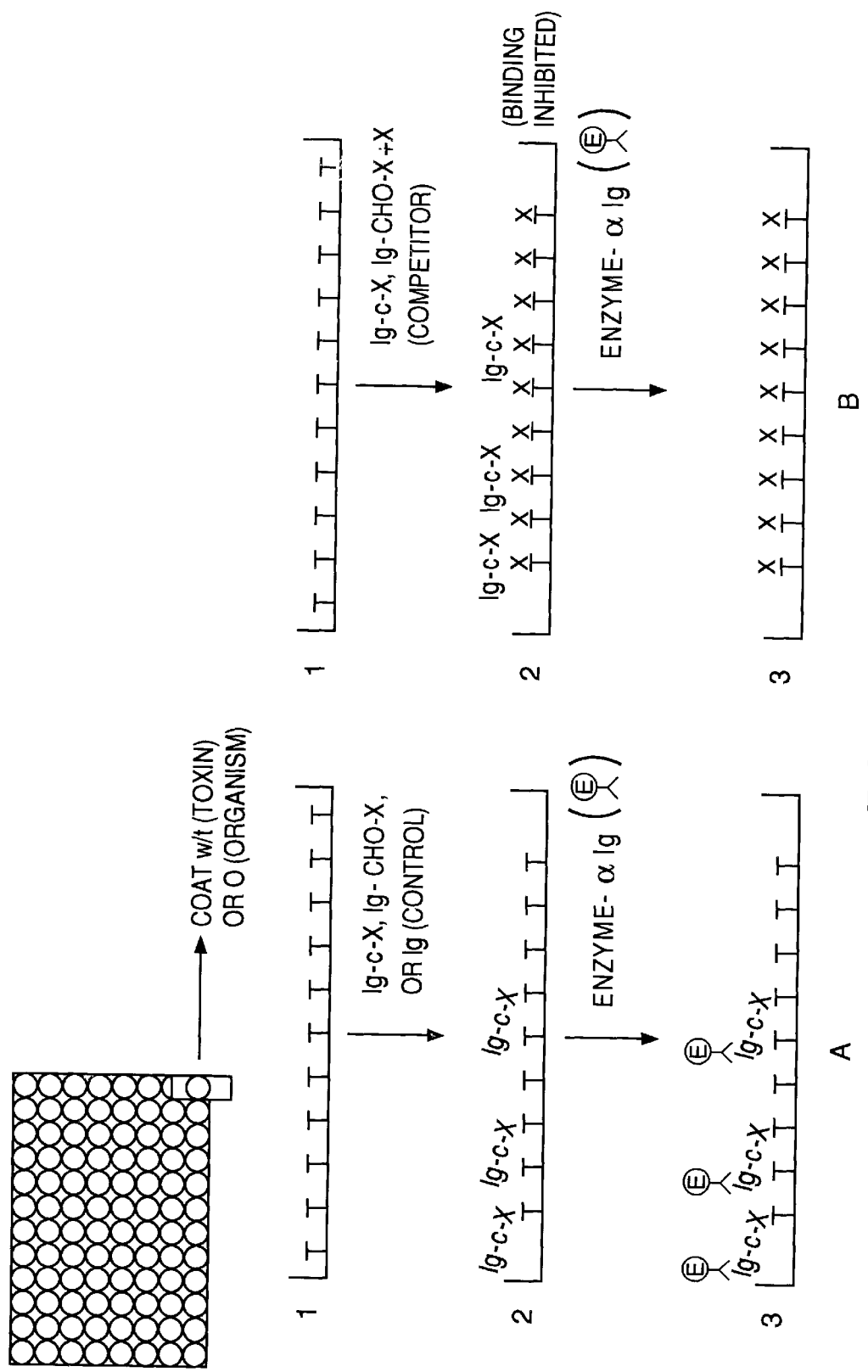
FIG. 4 describes solid phase assays for determining the level of binding of antibodiotics of the present invention. Step 1 shows toxin or organisms in a testing microwell. Step 2 schematically represents the binding of antibodiotic. Step 3 schematically shows the binding of secondary reagents.

FIGS. 2–4 outline the methods by which new antibiotics can be screened for use as compounds for conjugation with immunoglobulins. The "Screening Modes" consist of the following temporal steps:

Mode I: Conjugate the antibiotic to a cross-linker only and then assess for inhibition of organism growth in liquid culture and on a disc inhibition lawn assay.

Mode IIA: Conjugate the antibiotic via the cross-linker to immunoglobulin and then assess for binding to bacteria and bacterial toxin by a solid phase assay.

Mode IIB: Conjugate the antibiotic to immunoglobulin without the use of a cross-linker (e.g., periodate oxidation of the carbohydrate groups ["CHO"] of IgG) and then assess for binding to bacteria and bacterial toxin by a solid phase assay.

Mode III: Check specificity of the antibodiotic by inhibition of bacterial toxin binding with the antibiotic.

Mode IV: Assess the antibodiotic for inhibition of organisms growth in liquid culture.

By using this approach, a new antibiotic ("X") can be evaluated for use in the present invention. That is to say, antibiotic X is initially evaluated in Mode I. In this Mode, X is only conjugated to a cross-linker "c" to create "X-c"; this compound is then added to a liquid or solid phase culture. By creating only part of antibodiotic, the question of compatibility with immunoglobulin is avoided; Mode I only addresses compatibility of "X" with the conjugation chemistry. The assay is performed and the results are compared to an identical assay of unconjugated antibiotic X.

For the lawn assay comparison in Mode I, an agar-filled petri dish is streaked with the organism (Step 1, FIG. 2). A small filter-paper disc containing a known amount of antibiotic X or X-c is placed on the agar surface and allowed to diffuse into the medium over an 18- to 24-hr period (Step 2, FIG. 2). After this incubation, a zone of growth inhibition is apparent with X and this is compared to the zone (if any) achieved with X-c (Step 3, FIG. 2).

Alternatively for Mode I, known concentrations of X or X-c are diluted in broth in a test tube, which is then inoculated with an organism susceptible to X (FIG. 3). After incubation, the concentration that inhibits growth (i.e., no visible growth by turbidity) is determined, i.e., the minimum inhibitory concentration ("MIC") is established (FIG. 3A). To assess for bactericidal activity, an aliquot is taken from a tube showing bacteriostatic activity, and this aliquot is added to agar plates (FIG. 3B). If growth occurs, then the agent is bacteriostatic; if no growth occurs, the agent is bactericidal. The minimal bactericidal (lethal) concentration is the lowest concentration of X-c or X that produces a 99.9% reduction in organisms from the original inoculum of approximately 100,000 organisms. In this manner the minimum bactericidal concentration ("MBC") is established [I. S. Snyder and R. G. Finch in *Modern Pharmacology*, 2d Ed., (C. R. Craig and R. E. Stitzel, eds.), Little, Brown and Company, Boston, pp. 631–640 (1986); J. E. Conte, Jr. and S. L. Barriere, *Manual of Antibiotics and Infectious Diseases*, 6th Ed., Lea and Febiger, Philadelphia, pp. 135–152 (1988)].

When comparing X-c with X, some reduction in activity is expected. However, the more potent X is, the greater the reduction in X-c activity permissible. Overall, a range of 0.01 to 50 µg/ml for both the MIC and the MBC is practical.

If the activity of X-c is good, it is further evaluated in Mode IIA. If the activity of X-c is poor, X is evaluated in Mode IIB. Both Modes IIA and IIB contemplate covalent attachment; Mode IIA uses a cross-linker to create "X-c-Ig", while Mode IIB does not use a cross-linker and generates "X-CHO-Ig." In both cases, the antibody-antibiotic conjugate, or simply the "antibodiotic", is assayed on a solid phase assay such as shown schematically in FIG. 4.

Toxin or organisms may be used in the solid phase assay to coat a microwell or other appropriate surface (Step 1, FIG. 4A). The antibodiotic is then added to test for binding (Step 2, FIG. 4A). Standard washing procedures are used to avoid non-specific binding. The antibody portion of the conjugate may thereafter serve as a target for secondary reagents (e.g., goat anti-human IgG antibody having an enzyme reporter group such as horseradish peroxidase) (see  in Step 3, FIG. 4A). An appropriate substrate for the enzyme may then be added (not shown) to generate a colorimetric signal.

Where toxin is used in the solid phase assay, X-c-Ig binding may be compared with that of X-CHO-Ig. Where the organism is used, care must be taken that binding is not via the Fc receptor of Ig. Unconjugated Ig can be used as a control for this purpose.

To avoid any binding due to denaturation or other artifact, conjugates showing reactivity in Mode IIA or Mode IIB should be evaluated in Mode III. As shown in FIG. 4B, this simply involves adding free antibiotic to show that it will compete specifically for binding.

The next portion of the evaluation involves testing the antibody-antibiotic conjugate for growth inhibition and/or bactericidal activity (Mode IV). This is the same assay as shown in FIG. 2, the difference being that now the complete conjugate X-c-Ig (or X-CHO-Ig) is evaluated rather than just the antibiotic (X-c).

Both X-c-Ig and X-CHO-Ig may show good toxin binding in Mode II but poor anti-bacterial activity in Mode IV. If the specificity of the binding is nonetheless confirmed in Mode III, these compounds are candidates for diagnostic reagents. Alternatively, they may be used in vivo simply to bind free toxin and thereby reduce toxin load.

Thoughtful consideration of the results of each of these steps allows any antibiotic to be analyzed for potential use in the form of an antibodiotic. Following these in vitro tests, the antibiotic can then be evaluated in vivo for reduced toxicity and pharmacokinetics.

II. Antibodiotic In Vitro and In Vivo Efficacy

A. In Vitro Reactivity of the Fc Region

In the previous section, the key question was whether the antibiotic portion of the conjugate shows the same or similar reactivity as the native antibiotic. However, it must be emphasized that immunoglobulin is not simply an inert carrier. The Fc portion of the antibody can mediate pathogen elimination by two mechanisms that are distinct from the effects of the antibiotic. First, it is known that the Fc region can activate the classical pathway of complement, ultimately resulting in the lysis of the organisms. Second, binding of the conjugate to bacteria can lead to the ingestion or opsonization of the organism by recognition of the Fc region by phagocytes (e.g., macrophages) and/or lysis by killer cells. [See L. E. Hood et al., *Immunology*, 2d Ed., The Benjamin/Cummings Publishing Company, Inc., Menlo Park, pp. 339–340 (1984).]

The present invention contemplates antibody-antibiotic conjugates with the capability of binding Fc receptors on phagocytes. It is preferred that in competition binding, the binding of the antibody-antibiotic conjugates of the present invention to such cells is substantially similar to that of normal IgG.

The present invention contemplates antibody-antibiotic conjugates which, while not activating complement systemically, are capable of binding complement to facilitate pathogen killing. Furthermore, conjugates are contemplated which bind phagocytes via the Fc region to facilitate pathogen elimination.

B. Efficacy of the Conjugate In Vivo

Regardless of the manner in which the conjugate is used in vivo (acute, prophylactic, etc.), the conjugate will be in a background of the entire repertoire of host immune mediators. These immune mediators include, of course, humoral immune mediators such as endogenous antibody to bacteria and their toxins.

In this regard, several studies have suggested a causal relationship between a person's humoral immune status and the susceptibility to gram-negative infections. In patients who survived *Pseudomonas aeruginosa* septicemia, both total IgG levels and the circulating titer of core antigen-specific anti-LPS levels were significantly higher than in those patients who succumbed [M. Pollack et al., J. Clin. Invest., 72:1874–1881 (1983)]. Similarly, a correlation has been found between the titer of IgG against the patient's infecting organism and the frequency of shock and death [S. H. Zinner and W. R. McCabe, J. Infect. Dis., 133:37–45 (1976)].

These studies suggest that patients at risk of gram-negative sepsis and endotoxemia may be so because of weakened humoral immune defenses. For this reason, the present invention contemplates, in one embodiment, determining the immune status of the host prior to administration of the antibodiotic. This determination can be made by screening potential risk groups for total and endotoxin core antigen-specific IgG and IgM levels [B. J. Stoll et al., Serodiagnosis and Immunotherapy 1:21–31 (1987)]. Screening is believed to be particularly important with the elderly, full-term and pre-term neonates [W. Marget et al., Infection 11:84–86 (1983)], patients with malignancies [C. Stoll et al., Infection 13:115–119 (1985)], abdominal surgery candidates, individuals under long-term catheterization or artificial ventilation, and burn and other trauma victims.

Where the immune status is poor (e.g., low total IgG levels and low levels of anti-bacterial antibodies), the efficacy of the antibody-antibiotic conjugate is expected to be most dramatic. Where the host's immune status is good, use of the conjugate will support the endogenous anti-bacterial defenses.

III. Antibodiotic Applications

A. Prophylactic Use in Humans

The diagnosis of sepsis is problematic. First, the development of sepsis does not require the persistent release of toxin into the circulation; thus, many patients who die of sepsis are never shown to be bacteremic [R. C. Bone, Ann. Intern. Med., 115:457–469 (1991)]. Second, even if bacteria are detected, the amount of time needed for this detection is often too great to be practical.

For these reasons and others, the present invention contemplates the use of antibodiotics in humans prior to the onset of symptoms. In particular, the present invention contemplates the use of antibodiotics as a prophylactic in patients with a high risk for infection as well as sepsis.

High risk patients include surgical patients (particularly elderly surgical patients), low birth weight infants, and burn and trauma victims. Trauma patients are particularly difficult to examine because of the multitude of invasive procedures that they have undergone. Trauma patients are also typically hooked up to a number of devices, including intravascular lines, mechanical ventilators and Foley catheters. While every attempt is made to change intravascular lines, this is frequently impossible because of the extent of trauma and the lack of venous accessibility [E. S. Caplan and N. Hoyt, Am. J. Med., 70:638–640 (1981)].

Most patients with multiple trauma have fever as well as increased white counts due to the stress of the trauma itself. The classic indicators of infection, therefore, may or may not reflect an ongoing infection.

Because of this, current clinical practice involves treating patients with antibiotics only for specific indications, and for as short a period of time as possible. Generally, the average course for any documented infection is seven to ten days. Prophylactic antibiotics are used in only three instances: open fractures, penetrating abdominal injuries and penetrating facial injuries in which there is injury to the respiratory mucosa. Even in these situations, antibiotics are used for only three to five days, depending on the injury.

By contrast, the present invention contemplates treating all trauma patients prophylactically with antibodiotics. Because of the reduced toxicity of the conjugates and their longer residence time in the circulation, the present invention contemplates administering antibodiotics immediately to the trauma patient upon admission. Indeed, the antibodiotics may successfully be used at the first moment that clinical care is available (e.g., emergency mobile care).

Rather than the short (i.e., three to seven day) period of protection provided by using native antibiotics, the use of the antibiotic-antibody conjugates of the present invention should protect the trauma patient during the entire period of risk.

Burn patients have many of the same problems with respect to the diagnosis and therapy for infection. Since the magnitude of thermal injury is related to the level of trauma in a burn victim, this even becomes more of a problem with acute cases.

It is reported that septicemia appears in the blood cultures of burn patients almost four days after a septic state [M. Meek et al., J. Burn Care Rehab., 12:564–568 (1991)]. Consequently, therapy with the conjugates of the present invention is particularly appropriate immediately after the burn injury as a means of preventing a septic reaction. Furthermore, in severe cases, consideration should be given to the topical administration of antibodiotics to prevent wound sepsis.

Importantly, burn victims are exposed equally to both gram negative and gram positive organisms. Burn victims are particularly good candidates for therapeutic preparations having bactericida activity for both gram-positive and gram-negative organisms. This includes conjugates using a single antibiotic with reactivity for both groups of organisms (e.g., antibiotics such as a cephalosporin or penicillin) and well as therapeutic "cocktail" preparations comprising: (i) a first conjugate consisting of a first antibiotic covalently bound to non-specific immunoglobulin; and (ii) a second conjugate consisting of a second antibiotic covalently bound to non-specific immunoglobulin (e.g., where the first antibiotic is polymyxin and the second antibiotic is bacitracin). Alternatively, two different antibiotics can be covalently bound to the same immunoglobulin molecule.

The use of blood cultures and the like has also been shown to be unreliable in the diagnosis of neonatal sepsis; indeed, in practice they appear to have little or no influence on antibiotic therapy decision making for at risk infants [T. J. Zuerlein et al., Clin. Ped., 29:445–447 (1990)]. For this reason, the conjugates of the present invention can be applied with great advantage, i.e., antibiotics can be used without the concern of toxicity and the longer circulating half-life allows for antibiotic therapy without necessarily prolonging hospitalization.

Finally, surgical patients also represent a risk group where the conjugates of the present invention can be used successfully. Current practice involves the prophylactic use of antibiotic in a very narrow category of cases (e.g., elective colorectal procedures, cholecystectomy, hysterectomy and Caesarean sections) [R. L. Nichols in *Decision Making in Surgical Sepsis*, B. C. Decker, Inc., Philadelphia, pp. 20–21 (1991)]. One to two grams of a broad-spectrum antibiotic are administered intravenously at the induction of anesthesia. An additional dose may be given during an extensive procedure or post-operatively but prophylaxis beyond 24 hours is not indicated. Twenty-four hours of antibiotic prophylaxis is considered to be sufficient to control contamination. Continuance of antibiotic prophylaxis beyond 24 hours is an added expense, particularly when using an antibiotic with short serum and tissue half-lives. Most importantly, continuation of antibiotic prophylaxis also runs an excessive risk of drug toxicity and emergence of resistant strains.

By contrast, the longer serum half-life of the conjugates of the present invention provide extended protection against sepsis without the expense of multiple dosing. Furthermore, since the distribution of immunoglobulin is predominantly to vascular compartments, the use of the conjugates of the present invention may reduce the risk of disruption of endogenous flora. Consequently, the conjugates of the present invention may be used liberally (e.g., in more categories of surgical procedures).

B. Acute Therapy in Humans

As noted previously, the present invention also contemplates the use of antibodiotics in a therapeutic preparation for acute treatment. In this case, treatment involves administration of the antibody-antibiotic conjugates after infection is detected and/or sepsis is suspected.

Evidence suggestive of gram-negative infection includes the following: (1) core temperature higher than 38° C. or lower than 35° C.; (2) peripheral blood leukocyte count greater than $12 \times 10^9/L$ or less than $3 \times 10^9/L$ (not due to chemotherapy), or at least 20% immature forms; (3) growth of gram-negative pathogens from a blood culture drawn within the preceding 48 hours; or (4) documented or suspected site of gram-negative infection.

Current medical practice accepts sepsis as having no specific pharmacotherapy available [R. L. Greenman et al., JAMA 266:1097–1102 (1991)]. A systemic septic reaction is characterized by at least one of the following: arterial hypotension (systolic blood pressure <90 mm Hg or an acute drop of 30 mm Hg); metabolic acidosis (base deficit >5 mEq/L); decreased systemic vascular resistance (systemic vascular resistance <800 dyne/s cm5); tachypnea (respiratory rate >20/min or ventilation >10 L/min if mechanically ventilated); or otherwise unexplained dysfunction of the kidney (urine output <30 mL/h), or lungs.

It must be stressed that the antibodiotics of the present invention should ideally be used prior to a systemic infection, if possible. For example, the conjugates can be administered immediately after bacteremia or fungemia is detected. Similarly, conjugate can be administered where there is an obvious sign of infection at a particular site (e.g., sinusitis, meningitis, respiratory or urinary tract infections, etc.).

Primary bacteremia is typically defined as two or more blood cultures with the same organism occurring in a patient with no other obvious site of infection. Sinusitis is diagnosed in a patient who has at least two of the following: purulent nasal discharge, roentgenographic evidence of sinusitis or purulent material which may be aspirated from the sinuses.

The lower respiratory tract is a common site of infection. Pneumonia in the intubated patient is diagnosed in a patient when there is fever, leukocytosis and a Gram stain with many polymorphonuclear leukocytes. In addition, the patient has new infiltrate that did not clear with intensive physical therapy. This last criteria helps to rule out atelectasis.

C. Veterinary Care

Septicemia and sepsis are by no means limited to human beings. Infection by gram-negative bacteria accounts for significant morbidity and mortality in neonatal calves [D. D. Morris et al., Am. J. Vet. Res., 47:2554–2565 (1986)]. Interestingly, humoral immune status is again related to susceptibility to sepsis and this is largely dependent on passive transfer from colostrum. For this reason, the present invention contemplates, in one embodiment, determining the immune status of the animal prior to administration of the antibodiotic. This determination can be made by screening neonatal calves for total circulating immunoglobulin in their serum (e.g., by ELISA).

Where the immune status is poor (e.g., low total IgG levels), the conjugate should be used prophylactically. Where the animal's immune status is good, use of the conjugate may be needed for acute therapy for gram-negative bacterial sepsis, which remains prevalent in neonatal calves even with high antibody levels.

The present invention contemplates the treatment of other animals as well. Among foals less than 10 days of age in critical distress, sepsis is the most serious problem [A. M. Hoffman et al., J. Vet. Int. Med., 6:89–95 (1992)]. Symptoms highly indicative of sepsis risk include weakness, metabolic disturbance and dehydration. In one embodiment, the invention contemplates using antibodiotics for prophylactic treatment of foals less than 10 days of age having these indicators.

While positive blood cultures are found in less than half of the cases, those animals found positive have a very poor chance of survival. The present invention therefore contemplates using antibodiotics for acute treatment of animals showing evidence of septicemia.

IV. Therapeutic Preparations and Combinations

The present invention contemplates using therapeutic compositions of soluble antibodiotics. It is not intended that the present invention be limited by the particular nature of the therapeutic preparation. For example, such compositions can be provided together with physiologically tolerable liquid, gel or solid carriers, diluents, adjuvants and excipients. In addition, antibodiotics may be used together with other therapeutic agents, including unconjugated immunoglobulin.

As noted above, these therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

With respect to the mode of administration, the antibodiotics may be employed for intravenous, intramuscular, intrathecal or topical (including topical ophthalmic) administration. Formulations for such administrations may comprise an effective amount of antibodiotic in sterile water or physiological saline.

On the other hand, formulations may contain such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared as injectables, either as liquid solutions or suspensions; solid forms suitable for solution in, or suspension in, liquid prior to injection may also be prepared.

The antibodiotics of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Where repeated administrations are required, it may be beneficial to first clear any anti-hapten antibodies by administering free antibiotic. This can then be followed by administration of the antibodiotic.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); ng (nanograms); L (liters); ml (milliliters); $\mu$l (microliters); cm (centimeters); mm (millimeters); $\mu$m (micrometers); nm (nanometers); °C. (degrees Centigrade); ELISA (Enzyme-Linked Immunosorbent Assay); Baxter (Deerfield, Ill.); BBL (Becton Dickinson Microbiology Systems, Cockeysville, Md.); Falcon (Lincoln Park, N.J.); Lee (Lee Laboratories, Grayson, Ga.); Pierce (Pierce Chemical Co., Rockford, Ill.); Scientific Products (McGraw Park, Ill.); Sigma (Sigma Chemical Co., St. Louis, Mo.).

EXAMPLE 1

Attachment of an Antibiotic to Human IgG Using a Carbodiimide Cross-linker

This example describes attempts to attach antibiotics to a carrier, i.e., in this case antibodies. In this regard, K. Hanasawa et al. describe the attachment of PMB to an immobilized fiber via carbodiimide chemistry [Surg. Gyn. & Ob., 168:323–331 (1989)]. In this example, the ability of a carbodiimide cross-linker to conjugate polymyxin B (PMB) to human IgG was analyzed.

1-ethyl-3(3-dimethylaminopropyl)carbodiimide hydrochloride (EDC) cross-links proteins and peptides between amine and carboxylic acids. The example involved: (a) EDC-mediated cross-linking of PMB and IgG; and (b) enzyme-linked immunoassay (ELISA) of conjugate binding to LPS.

a) EDC-Mediated Cross-linking of PMB to IgG

In this and in all examples, measures were taken to make glassware, solutions, and other materials and reagents pyrogen-free because adventitious pyrogen (LPS) could inhibit conjugation reactions, absorb PMB or conjugates, or block the activity of PMB conjugates.

Human IgG (Sigma) and PMB (Sigma) were each dissolved at a concentration of 8 mg/ml in pyrogen-free MES (2-[N-Morpholino]ethanesulfonic acid) buffer (0.2M MES, 0.09 M NaCl pH 4.7). 0.5 ml of each solution were mixed and 0.15 ml of the mixture was incubated with 0.15 ml of either 0.4 M EDC, 0.2 M EDC, 0.1 M EDC (Pierce), or control solution in MES buffer for 2 hrs at room temperature. The reactions were stopped by the addition of 2.7 ml of TBS (50 mM Tris-HCl, 150 mM NaCl, pH 7.2). The five mixtures were dialyzed separately (molecular weight cut-off of dialysis tubing 12-14,000, Scientific Products) at 4° C. against four changes of 1500 ml of PBS over a 36 hr period. The samples containing human IgG at 0.2 mg/ml were stored at 4° C.

b) Enzyme-Linked Immunoassay of EDC-PMB Conjugate Binding to LPS

In order to determine whether the attachment of PMB facilitated the binding of IgG to LPS, a simple indirect binding assay was performed. To each well of a 96-well microtiter plate (Falcon), 100 µl of a 2.0 µg/ml solution of *E. coli* 0111:B4 LPS (Sigma) in PBS was coated, except for those control wells in which PBS but no LPS was added. After an overnight incubation at 4° C., the coating solutions were decanted and all wells were washed three times with PBS. The remaining antigen-binding sites were blocked by the addition of 100 µl of PBS containing 5 mg/ml bovine serum albumin (BSA, Sigma) for 2 hrs at room temperature. After decanting the blocking solution, samples of the conjugates prepared in step (a) above were diluted in PBS containing 1 mg/ml BSA to an initial concentration of 10 µg/ml IgG followed by five-fold dilutions. A positive control antiserum of commercially prepared rabbit anti-*E. coli* 0111:B4 antiserum (Lee Laboratories, Lot M25082) was initially diluted 1:100. One hundred (100) µl of each sample was incubated in duplicate for two hours at room temperature and the plates were washed three times with BBS-Tween 20 (0.1 M boric acid, 0.025 M Na borate, 1.0 M NaCl, 0.1% Tween 20, pH 8.3), followed by two washes with PBS-Tween 20 (0.1% Tween 20 (v/v)), and finally, two washes with PBS.

In order to detect bound antibodies, the wells incubated with the human antibody conjugates were incubated with 100 µl of a 1:500 dilution of goat anti-human IgG (whole molecule)-alkaline phosphatase conjugate (Sigma) and the wells incubated with the rabbit serum were incubated with 100 µl of a 1:500 dilution of goat anti-rabbit IgG (whole molecule)-alkaline phosphatase conjugate (Sigma) for 2 hours at room temperature. The secondary antibody solutions were discarded, the plates were washed with BBS-Tween 20, and PBS-Tween 20 as above and then twice with 50 mM $Na_2Co_3$, 10 mM $MgCl_2$, pH 9.5. After 45 minutes at room temperature, the absorbance of each well was measured at 410 nm on a Dynatech MR700 plate reader using diluent control wells as blanks. Tables 6 and 7 show the results for the rabbit control serum and EDC-conjugates.

The results in Table 6 show that the positive control serum, as expected, bound to LPS-coated wells in a specific manner. This validates the ELISA design as capable of detecting LPS binding antibodies.

TABLE 6

Binding of Rabbit anti-*E. coli* 0111:B4
Antiserum to *E. coli* 0111:B4 LPS

| Serum Dilution | LPS Coated | No Antigen |
|---|---|---|
| 1:1 | 1.801 | 0.032 |
| 1:5 | 1.817 | 0.028 |
| 1:25 | 1.648 | 0.024 |
| 1:175 | 0.308 | 0.026 |
| 1:625 | 0.070 | 0.027 |
| 1:3125 | 0.021 | 0.028 |
| 1:15,625 | 0.014 | 0.018 |

TABLE 7

Binding of EDC-Mediated Human IgG-PMB
Conjugates to *E. coli* 0111:B4 LPS

| Conjugate IgG conc. (µg/ml) | EDC conjugation conc. (M) | | | | |
|---|---|---|---|---|---|
| | 0.2 | 0.1 | 0.05 | 0.025 | 0 |
| 5 | 0.638 | 0.369 | 0.306 | 0.464 | 0.015 |
| 1 | 0.010 | 0.012 | 0.026 | 0.054 | 0.008 |
| 0.2 | 0 | 0 | 0.002 | 0.009 | 0.007 |
| 0.04 | 0 | 0 | 0 | 0.006 | 0.005 |

The results in Table 7 appear to indicate that EDC cross-linking caused the IgG-PMB to bind to the LPS. However, the titration of the conjugates drops off rather abruptly between 5 and 1 µg/ml. To verify that the observed binding is specific, it must be determined that the binding is inhibitable by PMB and antigen-dependent.

The ELISA described above was repeated; however, in this instance, a fixed concentration of the EDC-conjugate (10 µg/ml) that yielded the highest binding by ELISA was incubated with five-fold dilutions of polymyxin B (beginning with 10 mg/ml) and the LPS-binding activity was determined. In addition, the binding was tested in control wells containing no antigen. The results are shown in Tables 8 and 9.

TABLE 8

Specificity of EDC-Conjugates of IgG-PMB
Binding to LPS: PMB Inhibition Test

| PMB concentration (mg/ml) | 0.2M EDC-conjugate binding |
|---|---|
| 0 | 1.757 |
| 10 | 0.755 |
| 2 | 1.775 |
| 0.4 | 1.785 |
| 0.08 | 1.770 |
| 0.016 | 1.766 |
| 0.0033 | 1.775 |

TABLE 9

Antigen-Dependent Binding of
EDC-Conjugate of IgG-PMB to LPS

| Conjugate Conc. (µg/ml) | LPS Coated Wells | No Antigen Wells |
|---|---|---|
| 10 | 1.770 | 1.766 |
| 2 | 0.976 | 0.522 |
| 0.4 | 0.347 | 0.045 |
| 0.08 | 0.034 | 0 |
| 0.016 | 0.062 | 0 |

Since the binding of the conjugate is only inhibited at the very highest concentration of PMB tested and because the conjugate exhibits significant binding to wells that contain no antigen, it is clear that most of the binding observed is not specific. This may reflect an inappropriate type or number of bonds between PMB and IgG and, since IgG that was not treated with a cross-linker shows very little binding to LPS, it suggests that the cross-linking of the IgG molecule is causing nonspecific binding.

Clearly, carbodiimide chemistry does not work at a level which is practical. Indeed, it is evident that the interactions of the cross-linking reagent with the antibiotic are somewhat complex. It is to be remembered that three reactions are possible: PMB to PMB; IgG to IgG; and PMB to IgG. Only the latter reaction is productive.

EXAMPLE 2

Attachment of an Antibiotic to Human IgG Using a Disuccinimide Ester

In an attempt to remedy the difficulties observed with EDC conjugates, different cross-linkers and chemistries were investigated. Talmadge and Siebert describe the attachment of PMB via a hydroxysuccinimide ester reagent [J. Chrom., 476:175–185 (1989)]. Along the lines of this approach, this example examines the ability of a homobifunctional cross-linking agent suberic acid bis-(N-hydroxysuccinimide ester (DSS), which cross-links peptides and proteins via their amine groups, to conjugate PMB to IgG. The example involved: (a) DSS-mediated cross-linking of PMB and IgG; and (b) ELISA of conjugate binding to LPS.

a) DSS-Mediated Cross-linking of PMB to IqG

Pyrogen-free PBS was prepared in pyrogen-free water (Baxter), and stock solutions of human IgG (40 mg/ml) and PMB (20 mg/ml) were dissolved in pyrogen-free PBS. A 60 mM stock solution of DSS was prepared in 100% dimethylsulfoxide (DMSO). This solution was diluted to 6.0 mM DSS in PBS where some precipitation was noted. A stock solution of human IgG and PMB was prepared containing 20 mg/ml IgG and 10 mg/ml PMB in PBS. Five different conjugates were prepared by mixing two-fold dilutions of the stock DSS solution (0.15 ml) with a constant (0.15 ml) volume of the IgG/PMB stock solution. The five resulting DSS concentrations were 3.0 mM, 1.5 mM, 0.75 mM, 0.375 mM, and 0 mM DSS. After incubation for 1 hour at room temperature, the reactions were stopped by the addition of 2.7 ml of TBS. The five mixtures were dialyzed against PBS as described in Example 1 for the EDC conjugates. The resulting dialyzed conjugates contained a final concentration of 1 mg/ml IgG and were stored at 4° C.

b) ELISA of DSS Conjugated Binding to LPS

The ELISA was performed essentially as in Example 1(b) using the DSS conjugates at starting concentrations of 10 µg/ml and the same control rabbit anti-E. coli 0111:B4 antiserum. The results of the initial binding assay are shown in Table 10.

TABLE 10

Binding of DSS Conjugates of IgG-PMB to LPS

| Conjugate IgG | DSS concentration (mM) | | | | |
|---|---|---|---|---|---|
| conc. (µg/ml) | 3.0 | 1.5 | 0.75 | 0.375 | 0 |
| 10 | 0.098 | 0.032 | 0.04 | 0.011 | 0.015 |
| 2 | 0.026 | 0.003 | 0.007 | 0.005 | 0.007 |
| 0.4 | 0.011 | 0.001 | 0 | 0.002 | 0.002 |
| 0.008 | 0.010 | 0 | 0.002 | 0.004 | 0.004 |

The results indicate a low level of binding that is correlated with the concentration of DSS utilized. The specificity of this binding was then tested by examining the ability of PMB to inhibit binding and its dependence on antigen. The assays were performed exactly as described for the EDC conjugates in Example 1(b). The results are shown in Tables 11 and 12.

These results indicate that the DSS conjugate is binding somewhat non-specifically. The pattern of PMB inhibition is erratic in that the highest concentration shows no inhibition of binding but intermediate PMB concentrations do apparently inhibit.

TABLE 11

Inhibition of IgG-PMB Binding to LPS by Free PMB

| PMB conc. (mg/ml) | 3.0 mM DSS conj. of IgG-PMB (50 mg/ml) |
|---|---|
| 0 | 0.144 |
| 10 | 0.182 |
| 2 | 0.054 |
| 0.4 | 0.059 |
| 0.08 | 0.097 |
| 0.016 | 0.128 |
| 0.0033 | 0.213 |

TABLE 12

Antigen-Dependent Binding of
DSS Conjugate of IgG-PMB to LPS

| Conjugate conc. (µg/ml) | LPS coated wells | No antigen wells |
|---|---|---|
| 50 | 0.268 | 0.096 |
| 10 | 0.168 | 0.043 |
| 2 | 0.094 | 0.007 |
| 0.4 | 0.016 | 0.010 |
| 0.008 | 0.009 | 0 |

These results indicate some level of specific binding above a significant amount of non-specific binding. The binding of the control rabbit antiserum at 1:500 and 1:12,500 dilution was 1.766 and 0.38, respectively and was virtually all antigen-dependent. The relatively low level of binding here suggests that hydroxysuccinimide ester reagents such as DSS are not very effective cross-linkers for PMB and IgG. This could be due to the amine-amine chemistry employed, or due to properties of the DSS agent. We did note some insolubility of DSS in PBS; perhaps a more water soluble form of DSS would perform better. In addition, in both cases of the EDC and DSS conjugates, the PMB was exposed to a vast excess of cross-linker which could inhibit the ability of PMB to bind to LPS.

EXAMPLE 3

Two-Step Conjugation of PMB to IgG Using EDC and a Water Soluble Analogue of DSS In the previous two examples, cross-linkers were present in molar excess over IgG and were mixed simultaneously with both antibody and antibiotic. In this example, IgG was first modified with the cross-linker, the cross-linker removed, and then PMB added to the coupling reaction. In this way, the binding activity of PMB might be improved and the non-specific binding of the IgG reduced. In order to have an amine to amine coupling reagent that was more water soluble, $BS^3$ (Pierce), a water soluble analogue of DSS was employed. The example involved: (a) two-step conjugation of IgG-PMB with EDC; (b) two step conjugation of IgG-PMB with $BS^3$; and (c) ELISA of conjugate binding to LPS.

a) Two-Step Conjugation of IgG-PMB with EDC 0.75 ml of a 4 mg/ml IgG solution in MES buffer prepared as described in Example 1 was mixed with 0.75 ml of a 0.4 M EDC solution in MES buffer at room temperature for 2 hours. The unreacted cross-linker was removed by passing the 1.5 ml reaction mixture over a Sephadex G-10 (Pharmacia) column that was poured into a sterile 10 ml pipette and equilibrated with pyrogen-free MES buffer. The void volume was collected and the IgG content was determined by measuring the $OD_{280}$ of a 1:40 dilution of each fraction. The peak fraction containing 2.37 mg IgG/ml was divided into two fractions: 1.5 mg of PMB was added and dissolved in one volume; nothing was added to the other (control). After incubation at room temperature overnight, the reaction was stopped with TBS and the final IgG concentration adjusted to 0.2 mg/ml. Both samples were dialyzed as in Example 1(a) and stored at 4° C.

b) Two-Step Conjugation of IgG to PMB with $BS^3$ 0.75 ml of a 20 mg/ml IgG solution was mixed with 0.75 ml of a 0.6 mM $BS^3$ solution, each prepared in PBS and incubated at room temperature for 1 hr. Unreacted cross-linker was removed as in Example 3(a) above and the peak IgG fractions identified and pooled. Two equal fractions of IgG at 8.35 mg/ml were made and 7.5 mg of PMB was added and dissolved in one while nothing was added to the other. After overnight incubation at room temperature the reactions were stopped with TBS, the conjugates dialyzed and the final IgG concentration adjusted to 1.0 mg/ml.

c) ELISA of Conjugate Binding to LPS

This LPS-binding assay was performed as described in Example (1) except for the BBS-Tween 20 washes were eliminated and the Tween 20 concentration in the PBS-Tween 20 wash was lowered to 0.05% (v/v). The results are shown in Tables 13 and 14.

The 0.2 M EDC IgG-PMB conjugate exhibited a high level of binding but this was partly due to non-specific binding as evidenced by the binding to control wells containing no LPS. Further evidence of non-specific binding created by EDC cross-linking is in the conjugate containing no PMB which exhibited somewhat comparable levels of binding to the wells regardless of whether antigen was present.

TABLE 13

Binding of Two-step EDC Conjugates to LPS

| Conjugate IgG conc. | 0–2M EDC IgG · PMB conj. | | 0–2M EDC (no PMB) IgG control | |
|---|---|---|---|---|
| | LPS coated | No antigen | LPS coated | No antigen |
| 10 | 1.790 | 1.790 | 1.784 | 1.790 |
| 2 | 1.520 | 0.886 | 0.676 | 0.522 |
| 0.4 | 0.092 | 0.146 | 0.088 | 0.079 |
| 0.08 | 0.024 | ND | 0.028 | ND |
| 0.016 | 0.046 | ND | 0.030 | ND |

TABLE 14

Binding of Two-step $BS^3$ Conjugate to LPS

| Conjugate IgG concentration (µg/ml) | 6.0 mM $BS^3$ IgG-PMB | | 6.0M $BS^3$ IgG | |
|---|---|---|---|---|
| | LPS | No antigen | LPS | No antigen |
| 10 | 0.037 | 0.040 | 0.028 | 0 |
| 2 | 0.016 | 0 | 0.022 | 0 |
| 0.4 | 0.044 | 0 | 0.044 | 0 |
| 0.08 | 0.040 | ND | 0.076 | ND |
| 0.016 | 0.038 | ND | | ND |

The $BS^3$ conjugates exhibited no specific binding to LPS whatsoever at the concentrations tested. However, they did not exhibit much non-specific binding either and this cross-linker may not be as problematic as EDC in causing non-specific binding of IgG.

Given the low level of $BS^3$ conjugate background binding, the ELISA was performed again using higher concentrations of the conjugates and a tenfold higher concentration of LPS was coated onto the wells (2 µg LPS/well). This increased the assay sensitivity. The results shown in Table 15 indicate that the $BS^3$ conjugates do possess LPS-binding activity above background.

TABLE 15

More Sensitive Detection of $BS^3$
Conjugates of IgG-PMB Binding to LPS

| Conjugate IgG concentration (µg/ml) | 6.0 mM $BS^3$ IgG-PMB | | 6.0M $BS^3$ IgG (control) | |
|---|---|---|---|---|
| | LPS | No antigen | LPS | No antigen |
| 50 | 0.098 | 0.010 | 0.006 | 0.006 |
| 10 | 0.058 | 0.006 | 0.006 | 0.008 |
| 2 | 0.020 | 0.005 | 0.004 | 0.004 |
| 0.4 | 0.004 | 0.005 | 0.004 | 0.004 |
| 0.08 | 0.005 | ND | 0.004 | ND |

Together, the results of these two-step conjugations described in this example indicate that EDC creates an unacceptable level of non-specific binding while $BS^3$, the water soluble analogue of DSS, effects a modest level of specific binding and causes very little non-specific binding in this two-step conjugation format. Additional two-step conjugation procedures using other cross-linkers were investigated to determine whether higher levels of LPS-binding activity could be achieved than those obtained with $BS^3$.

EXAMPLE 4

Two Step Conjugation of PMB to IgG Using an Amine to Sulfhydryl Coupling Chemistry with SMCC Because of the unsatisfactory results of previous examples in obtaining high specific-binding of IgG-PMB conjugates to PMB, an alternative cross-linking method was investigated using sulfosuccinimidyl 4-(N-maleimidomethyl)cyclohexane-1-carboxylate [sulfo-SMCC] in a three-step procedure similar to that of T. Kitagawa et al. [J. Assoc. Anal. Chem., (1985)]. The example involved: (a) three-step conjugation of PMB to reduced IgG with sulfo-SMCC; and (b) ELISA of conjugate binding to LPS.

a) Three-Step Conjugation of PMB to IgG

In the first step of this procedure, reactive thiol groups were created in the IgG by treatment with 2-mercaptoethanol. 4.0 mg of IgG was dissolved in 0.45 ml of pyrogen-free 0.4 M $NaPO_4$ pH 6.0. Fifty $\mu$l of 0.1 M 2-mercaptoethanol in 5 mM EDTA, 0.1 $NaPO_4$, pH 6.0 was added and incubated at 37° C. for 1.5 hours. The free 2-mercaptoethanol was separated by applying the 0.5 ml sample to a 5 ml Sephadex G-10 column equilibrated in 0.1 M $NaPO_4$, 5 mM EDTA pH 6.0 and the IgG containing fractions identified and pooled.

The second step of this procedure involved preparation of malemide-activated PMB. 1.5 ml of a 0.16 mg/ml PMB solution in 50 mM sodium borate buffer pH 7.6 (pyrogen-free) and 1.5 ml of a 0.46 mg/ml sulfo-SMCC (Pierce) solution in the same borate buffer were mixed (creating a final concentration of 0.053 mM of each reactant) and incubated at 30° C. for 60 minutes. This is the "SMCC-activated" PMB.

The third step of the procedure involved incubation of 0.65 ml of the reduced IgG with 0.65 ml of the SMCC-activated PMB.

In this manner, the concentration of the two reactants was 0.0265 mM PMB and 0.013 mM IgG (a 2:1 molar ratio). After incubation at 4° C. for 20 hrs, 8.7 $\mu$l of a fresh solution of 0.1 M 2-mercaptoethanol was added and incubated at room temperature for 20 minutes. The IgG concentration was adjusted to 1.0 mg/ml with an equal volume of PBS. Samples of the conjugates were purified by dialysis against two 800 ml volumes of PBS over a 20 hour period or by gel filtration on a Sephadex G-10 column equilibrated in PBS. A control reduced human IgG fraction was prepared from the reduced IgG pool and the three preparations stored at 4° C.

b) ELISA of Conjugate-Binding to LPS

The LPS binding assay procedure was the same as that described in Example 1(b) except that the LPS was coated at 2 $\mu$g/well, the BBS-Tween 20 washes were eliminated, and the Tween 20 concentration in the PBS-Tween 20 wash was lowered to 0.05%. The blocking solution and sample diluent were prepared using pyrogen-free PBS and low-endotoxin BSA (Sigma). The results are shown in Table 16.

TABLE 16

Binding of an SMCC Conjugate of IgG-PMB to LPS

| Conjugate IgG Concentration ($\mu$g/ml) | SMCC IgG-PMB | | SMCC IgG Control | |
|---|---|---|---|---|
| | LPS | No antigen | LPS | No antigen |
| 100 | 0.084 | 0.011 | 0.038 | 0 |
| 20 | 0.013 | 0 | 0.012 | 0 |
| 4 | 0 | 0.005 | 0 | 0 |
| 0.8 | 0 | 0.028 | 0 | 0 |
| 0.016 | 0 | 0 | 0 | 0 |

The SMCC IgG-PMB exhibited slightly higher binding to LPS than the control but the overall level of binding was far below that of the positive control rabbit anti-E. Coli 0111:B4 antiserum (1.097 at a 1:25,000 dilution). It is possible that reduced IgG possesses only a few thiol groups available for cross-linking and that higher concentrations of activated PMB might drive the reaction more effectively.

EXAMPLE 5

Conjugation of an Antibiotic to IgG Without Using a Bifunctional Cross-linker

In all of the previous examples, free bifunctional cross-linkers were employed in attempts to covalently attach the antibiotic polymyxin to IgG. The configurations failed to yield a conjugate with LPS-binding activity comparable to that of an immune serum. Because of the binding observed in the absence of antigen, there were probably conjugates having less than one active PMB molecule to each molecule of IgG. To investigate means of attaching antibiotics to IgG without the involvement of a bifunctional cross-linker, periodate oxidation of the carbohydrate groups of IgG [D. A. Handley, Eur. Patent Appl. Pub. No. 428486] was used to create amine-reactive aldehyde groups that could potentially react with PMB and be reduced to establish a stable covalent linkage.

The example involved: (a) periodate oxidation of IgG in pH 4.0 sodium acetate buffer; and (b) conjugation of polymyxin B to periodate oxidized IgG.

a) Periodate oxidation of IgG in pH 4.0 sodium acetate buffer was achieved by dissolving 5 mg human IgG in 1 ml of water and mixing this solution with 200 $\mu$l of sodium acetate pH 4.0 (0.3 g sodium acetate and 960 $\mu$l glacial acetic acid in 100 ml $H_2O$) and 200 $\mu$l of 0.2 M $NaIO_4$ [modification of J. W. Goding, *Monoclonal Antibodies: Principles and Practice*, Academic Press, New York, p. 84 (1986)]. After 15 minutes at room temperature in the dark, the periodate solution was removed by gel filtration on a P-10 column in 50 mM $Na_2CO_3$ pH 9.5.

b) Conjugation of periodate-oxidized IgG with PMB was carried out by adding 10 mg of PMB to the IgG prepared in (a) for 1 hour at room temperature followed by 100 $\mu$l of $NaBH_3CN$ (4 mg/ml) for another 1 hr and dialysis against PBS overnight at 4° C.

Inspection of the LPS binding activity (not shown) revealed that the conjugate prepared was inactive. These results suggest that the periodate-oxidation of IgG, without the use of a cross-linker, is an ineffective means of covalent conjugation of antibiotics to antibody.

EXAMPLE 6

The Derivatization of Antibiotics With Cross-linkers: Preservation of Antibiotic Activity A significant concern with either one-step or multi-step schemes for conjugating antibiotics to antibodies is whether the conjugation scheme reduces or inactivates antibiotic function. In order to determine the best cross-linker concentration for derivatization of PMB in a multi-step conjugation scheme, the effect of the concentration of cross-linker on antibiotic activity was determined (see discussion of Mode IA above). The example involved: (a) modification of PMB with SPDP and the separation of free cross-linker; and (b) assay of derivatized PMB antibacterial activity.

a) Modification of PMB with SPDP and the separation of free cross-linker was carried out by mixing three different molar ratios of SPDP (2:1, 3:1 and 4:1) to PMB. 2.1 mg, 3.15 mg or 4.2 mg of SPDP (Pierce) dissolved in dimethyl sulfoxide was added to 5 mg of PMB in 0.5 ml of 50 mM sodium borate, 300 mM NaCl pH 9.0 and incubated for 30 minutes at room temperature with occasional shaking. Free cross-linker was removed from each sample by chromatography on a 15 ml Swift desalting column equilibrated with PBS-EDTA. The peak fractions containing the derivatized PMB were collected and pooled.

b) Assay of derivatized PMB antibacterial activity was carried out in a disc inhibition assay (see FIG. 2). *E. Coli* HB101 was plated on Trypticase-Soy Agar (TSA; BBL) to create a confluent lawn of bacteria. One-quarter inch blank paper discs (BBL) were then applied to the surface of the lawn and 20 μl of each test solution applied. After incubation at 37° C. overnight, zones of inhibition surrounding the disc were noted. The results (not shown) indicate that PMB derivatized at 2:1 or 3:1 molar ratios of SPDP-PMB were still active whereas antibiotic derivatized at a 4:1 molar ratio was inactive. Therefore, derivatization of PMB with SPDP was carried out at ratios of SPDP to PMB of less than or equal to 3:1.

EXAMPLE 7

Conjugation of SPDP-PMB to IgG

Having determined an SPDP cross-linker concentration that preserved the antibiotic activity of polymyxin B in Example 6, conjugates were prepared between SPDP-PMB and IgG by reacting the derivatized antibiotic with IgG to which additional sulfhydryl (—SH) groups were added by activation with Traut's reagent.

The example involved: (a) derivatization of PMB with SPDP; (b) derivatization of IgG with Traut's reagent; (c) conjugation of Traut-IgG with SPDP-PMB; and (d) conjugate LPS-binding activity assessment.

a) Derivatization of PMB with SPDP was carried out by adding 7 μmoles of SPDP (2.1 mg) in 50 μl of dimethylsulfoxide to 10 mg of PMB in 1 ml of 50 mM sodium borate, 300 mM NaCl, pH 9.0 and incubating at room temperature for 30 minutes on a rotating shaker. The unconjugated cross-linker was removed by applying the sample to 15 ml Swift desalting column (Pierce) equilibrated with 20 mM NaPO$_4$, 150 mM NaCl, 1 mM EDTA, pH 7.2 (PBS-EDTA). Peak fractions were pooled and stored at 4° C.

b) Derivatization of IgG with Traut's reagent was carried out by adding a five-fold molar excess (100 μl of a 0.2 mg/ml stock) of Traut's reagent (Pierce) to 5 mg of IgG dissolved in 1 ml of 50 mM triethanolamine, 0.15 M NaCl, 1 mM EDTA, pH 8.0 and incubating under nitrogen for 45 minutes at room temperature. The excess Traut's reagent was removed by gel filtration on a P-10 column equilibrated with PBS-EDTA. The peak fractions were combined.

c) Conjugation of Traut-IgG with SPDP-PMB was carried out by adding 3.5 mg Traut-IgG and 2 mg SPDP-PMB (77 fold molar excess of PMB) and incubating for 18 hours at room temperature. The conjugates were separated from free SPDP-PMB by gel filtration on a P-10 column (50 ml) equilibrated with PBS-EDTA and the peak fractions containing the IgG were collected, pooled, and stored at 4° C.

d) Conjugate LPS-binding activity assessment was carried out by evaluating the ability of each conjugate in (c) to bind LPS in an ELISA assay (see FIG. 4). The results indicated that the Traut IgG-PMB conjugate possessed limited binding activity (not shown).

EXAMPLE 8

Conjugation of SPDP-PMB to SPDP-IgG

Having determined that Traut's reagent does not generate a conjugate with preserved antibiotic activity in Example 7, conjugates were prepared between SPDP-PMB and IgG by reacting the derivatized antibiotic with IgG to which additional sulfhydryl (—SH) groups were added by activation with SPDP.

The example involved: (a) derivatization of PMB with SPDP; (b) derivatization of IgG with SPDP; (c) conjugation of SPDP-IgG with SPDP-PMB; and (d) conjugate LPS-binding activity assessment.

a) Derivatization of PMB with SPDP was carried out as in Example 7.

b) Derivatization of IgG with SPDP was carried out by adding 20 μl of 20 mM SPDP to 10 mg of IgG in 1 ml of 50 mM sodium borate 300 mM NaCl, pH 9.0 and incubating 30 minutes at room temperature with shaking. The free cross-linker was removed by chromatography on a 15 ml Swift desalting column equilibrated in 100 mM sodium acetate, 100 mM sodium chloride pH 4.5. The peak fractions were collected and concentrated on Centriprep-30 concentration (Amicon). To this sample, 7.7 mg of dithiothreitol in 250 gl of 100 mM sodium acetate, 100 mM sodium chloride pH 4.5 was added and incubated at room temperature for 30 minutes. The sample was again applied to a 15 ml Swift desalting column equilibrated with PBS-EDTA and peak fractions with the highest OD$_{280}$ were collected, pooled, at concentrated on a Centriprep-30 concentrator (Amicon).

c) Conjugation of SPDP-IgG with SPDP-PMB was carried out by adding the following combinations of reactants:

5 mg SPDP-IgG and 2 mg SPDP-PMB (43 fold molar excess of PMB)

2 mg SPDP-IgG and 2 mg SPDP-PMB (107 fold molar excess of PMB)

and incubating for 18 hours at room temperature. The conjugates were each separated from free SPDP-PMB by gel filtration on a P-10 column (50 ml) equilibrated with PBS-EDTA and the peak fractions containing the IgG were collected, pooled, and stored at 4° C.

d) Conjugate LPS-binding activity assessment was carried out by evaluating the ability of each conjugate in (c) to bind LPS in an ELISA assay and comparing them with the Traut conjugate produced in Example 7. The results (FIG. 5) indicated that both SPDP-IgG-PMB conjugates possessed considerable activity—much higher activity than the Traut IgG-PMB conjugate.

EXAMPLE 9

Conjugation of PMB to IgG Using a Long Chain SPDP Cross-linker

Figure 6:
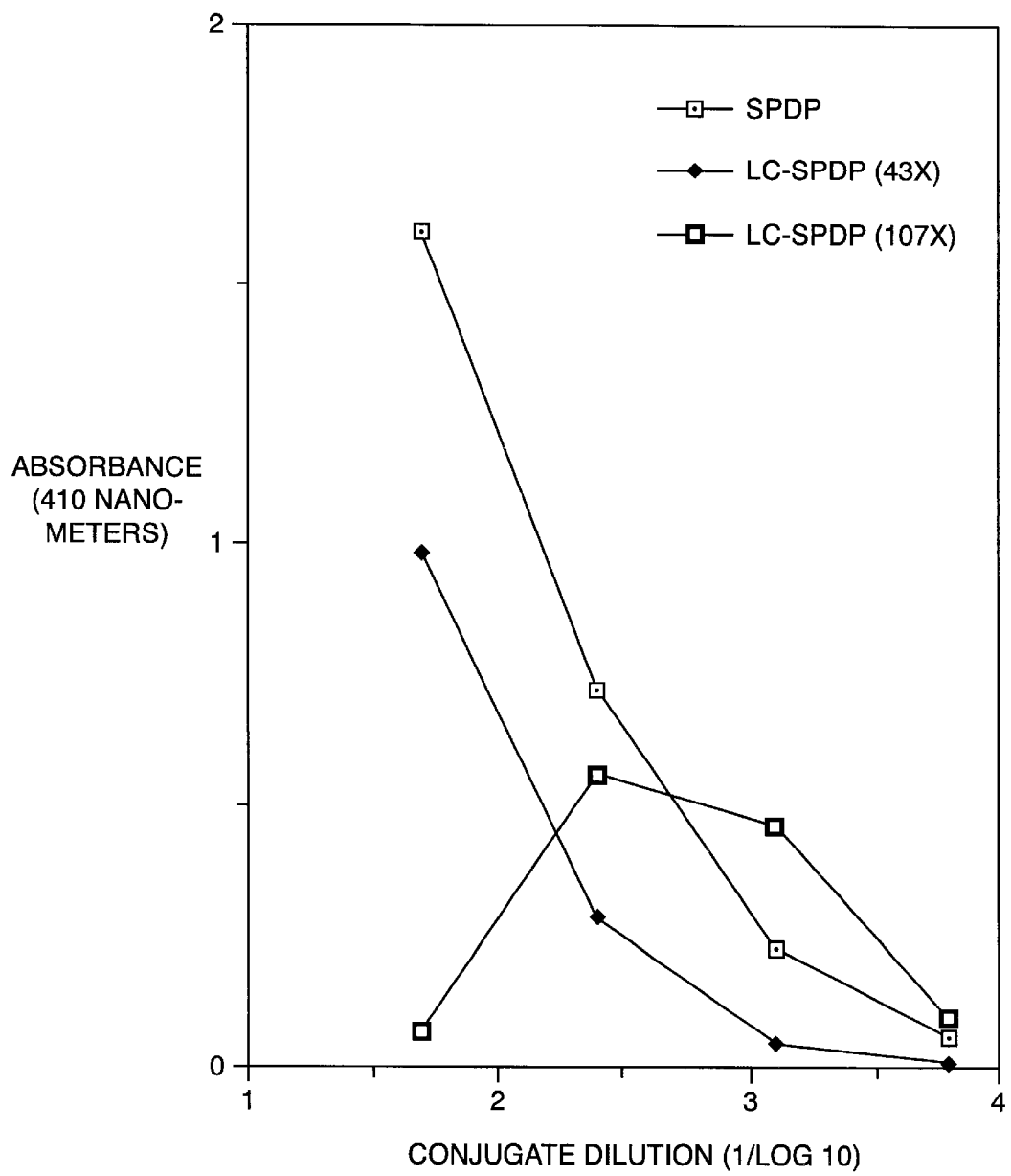
FIG. 6 shows additional conjugates of the present invention binding to LPS, as measured by ELISA.

Since SPDP proved to be an effective agent for the derivatization and cross-linking of IgG and PMB, a long chain form of SPDP (sulfo-LC-SPDP) was then examined to see if the addition of a larger spacer arm between the IgG and PMB enhanced the activity of the conjugate. The example involved: (a) derivatization of PMB with sulfo-LC-SPDP; (b) derivatization of IgG with sulfo-LC-SPDP; (c) conjugation of derivatized IgG with derivatized PMB; and (d) conjugate activity assessment by ELISA.

a) Derivatization of PMB with sulfo-LC-SPDP was carried out by adding 35 µl of a 9 mg/ml solution of sulfo-LC-SPDP to 10 mg of PMB in 1 ml of 50 mM sodium borate, 300 mM NaCl pH 9.0 and incubating for 30 minutes at room temperature. Free cross-linker was removed by gel filtration on a 1.5×35 cm P-2 column equilibrated in PBS-EDTA and peak fractions containing derivatized PMB were combined and stored at 4° C.

b) Derivatization of IgG with sulfo-LC-SPDP was carried out by adding 0.3 mg of sulfo-LC-SPDP to 10 mg of IgG in 50 mM sodium borate, 300 mM NaCl pH 9.0 and incubating for 30 minutes on a rotating shaker. The derivatized IgG was separated from free cross-linker on a 5 ml Swift desalting column (Pierce) equilibrated with 100 mM sodium acetate, 100 mM sodium chloride pH 4.5 and the peak fractions collected and pooled. This sample was then reduced by adding 7.7 mg of dithiothreitol in 250 µl of the same sodium acetate buffer and incubated for 30 minutes at room temperature. Excess reducing agent was removed by gel filtration on a 10 ml P-10 column equilibrated in PBS-EDTA. The peak fractions were collected and pooled.

c) Conjugation of derivatized IgG with derivatized PMB was carried out by adding 2.5 mg of IgG to 2.5 mg of PMB (107-fold molar excess of PMB) and 3.5 mg of IgG to 1.4 mg of PMB (43-fold molar excess of PMB), and incubating for 18 hours at room temperature. The IgG-PMB conjugate was separated from the rest of the reaction mixture on a 50 ml P-10 gel filtration column equilibrated with PBS-EDTA.

d) Conjugate activity assessment by ELISA indicated that the sulfo-LC-SPDP conjugates did not possess greater activity than the shorter SPDP molecule (FIG. 6).

EXAMPLE 10

Inhibition of Specific Binding of Antibodiotic to LPS by Free Antibiotic

Figure 5:
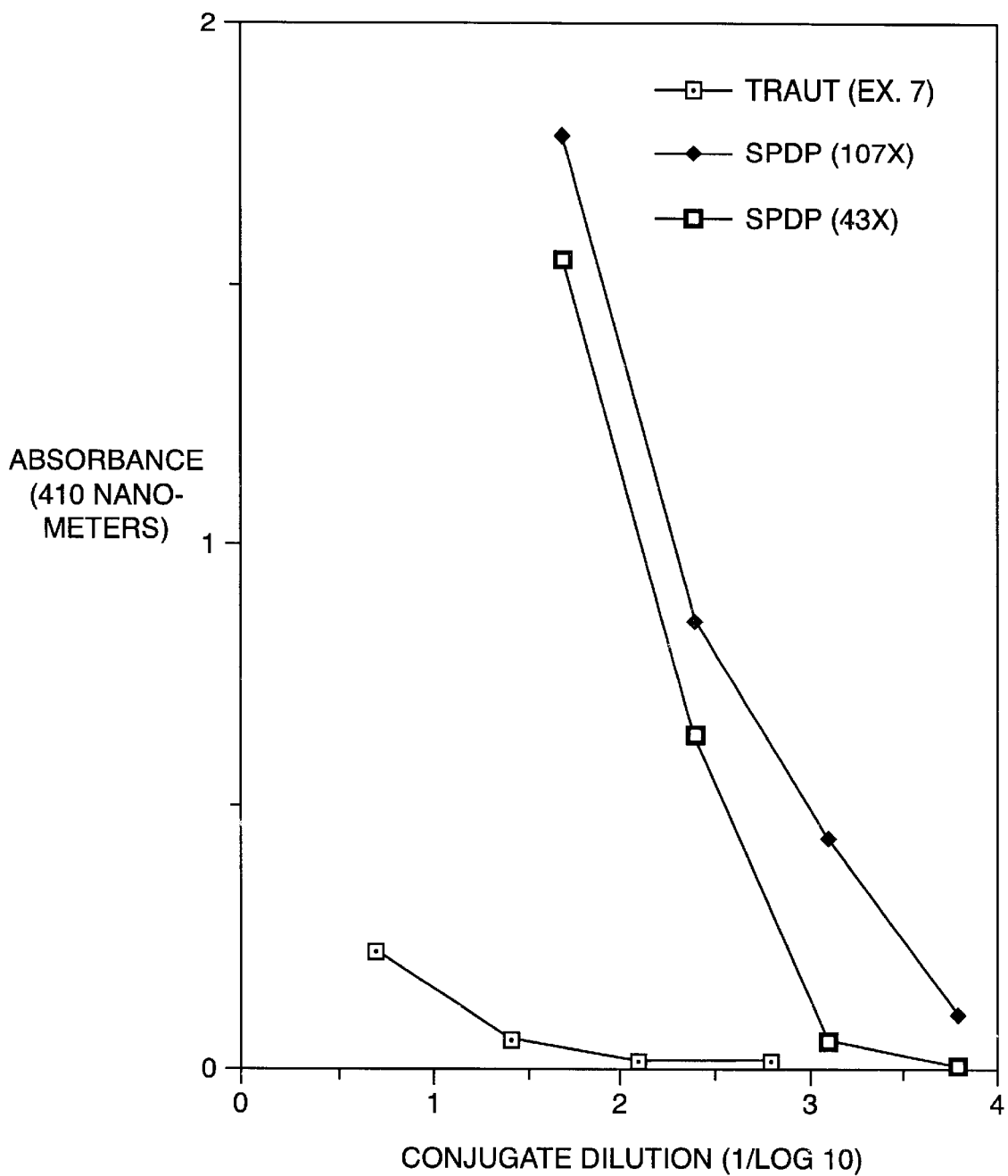
FIG. 5 shows conjugates of the present invention binding to LPS, as measured by ELISA.

In order to determine that the antibody-antibiotic conjugate binding observed in FIG. 5 is specific, free antibiotic was used to block conjugate binding (see mode III discussion, above). This example involved: (a) mixing of the antibodiotic with free antibiotic; and (b) assaying the degree of conjugate binding to LPS in the presence of different concentrations of free antibiotic.

a) Mixing of antibodiotic with free antibiotic was performed by adding an equal volume of a 1:125 dilution (32 µg/ml) of the SPDP IgG-PMB conjugate in PBS-Tween 20 (0.05%) containing 1 mg/ml BSA with polymyxin at 0–20 µg/ml in the same buffer. Two hundred (200) µl of this mixture containing 0–4000 µg of PMB and 3.2 µg of conjugate was then assayed for binding activity.

b) Assaying the degree of conjugate binding to LPS in the presence of different concentrations of free antibiotic was performed by adding 200 µl of the antibodiotic/free antibiotic mixture to wells of a 96-well microtiter plate that had been coated with 2 µg of E. coli 0111:B4 LPS and blocked as described in Example 1. The wells were washed, goat anti-human Ig-alkaline phosphatase was added, and the binding assayed quantitatively on a MicroELISA reader exactly as described in Example 1.

Figure 7:
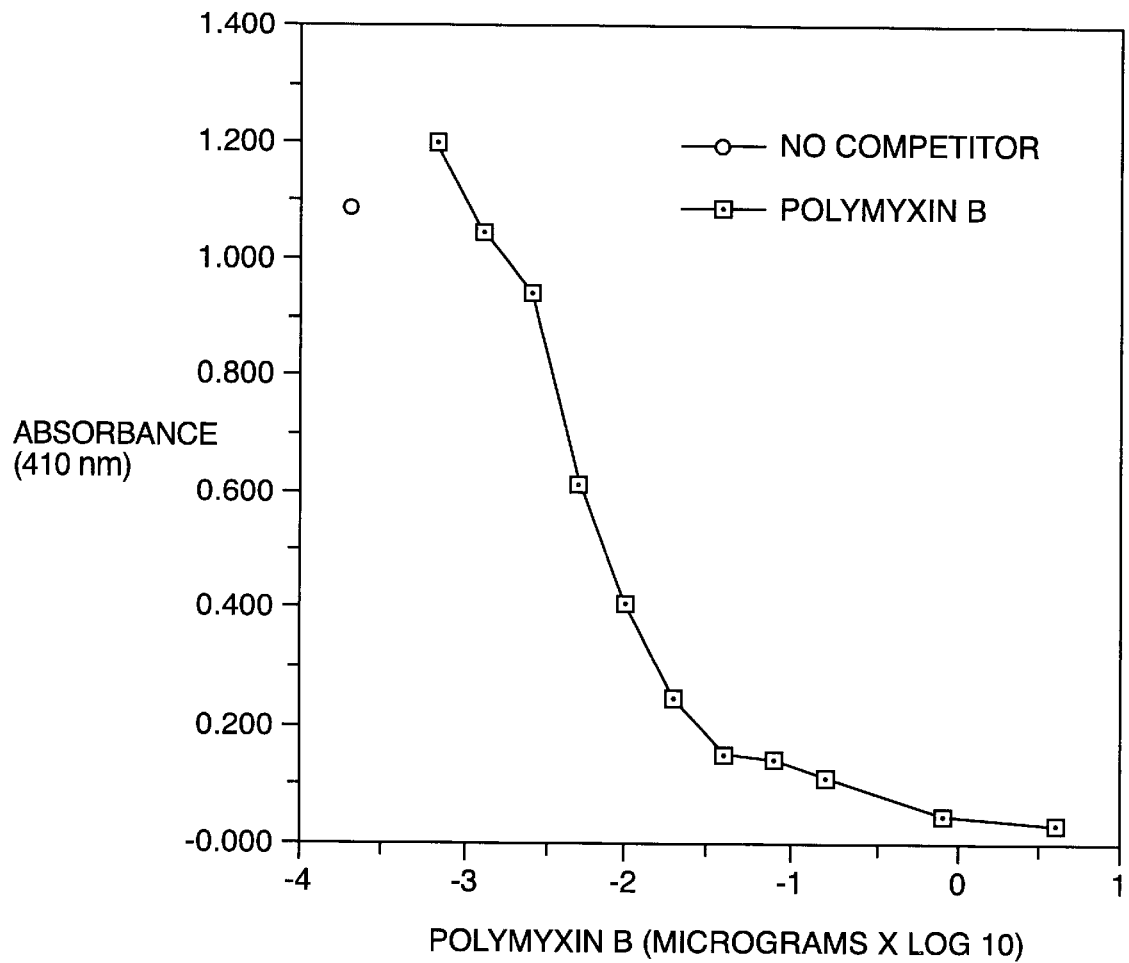
FIG. 7 shows inhibition of LPS binding of conjugates of the present invention using free polymyxin (PMB), as measured by ELISA.

The results are shown in FIG. 7 and demonstrate that free polymyxin competitively inhibits IgG-PMB binding to LPS. Clearly, the antibodiotic is binding specifically to LPS, (i.e., via the conjugated PMB moieties.

Inspection of the inhibition curve gives some indication of the extent of active PMB conjugation in that a 16 µg/ml solution of antibody ($1.1 \times 10^{-7}$M) is 50% inhibited in its binding to LPS by a concentration of 40 ng/ml PMB ($2.6 \times 10^{-8}$M). If one molecule of PMB was present on each PMB (making the PMB concentration on IgG equal to $1.1 \times 10^{-7}$) one would expect that an equilmolar concentration of free PMB would inhibit binding by 50%. Since it requires one fourth the concentration of free PMB to inhibit this antibodiotic, one may conclude that there is at least one, PMB molecule per four IgG molecules. In fact, since SPDP modified PMB has a four-fold lower antibiotic activity than free PMB, the actual degree of IgG conjugation with PMB is probably at least four-fold higher than that calculated above (i.e., there is probably at least one PMB conjugated to each IgG molecule).

EXAMPLE 11

Conjugation Using Periodate Oxidation of IgG in $NaPO_4$

In Example 5, a means of attaching antibiotics to IgG without the involvement of a bifunctional cross-linker (i.e., periodate oxidation of the carbohydrate groups of IgG) was attempted. This involved, in part, periodate oxidation of IgG in pH 4.0 sodium acetate buffer and failed to yield a conjugate with significant activity. Because this failure may have been due to the reaction conditions, different reaction conditions were explored. This example involves: (a) periodate oxidation of IgG in phosphate buffer; and (b) conjugation of polymyxin B to periodate oxidized IgG.

a) Periodate oxidation of IgG in phosphate buffer was achieved by dissolving 10 mg of human IgG in 1 ml of 50 mM $NaPO_4$ pH 7.2 and adding 0.011 g sodium metaperiodate (final concentration 50 mM). After 30 minutes at room temperature, the periodate solution was removed by gel filtration on a 10 ml P-10 gel filtration column equilibrated in 50 mM $NaPO_4$ pH 7.2. The peak fractions containing antibody were pooled and concentrated to 1.5 ml.

b) Conjugation of periodate-oxidized IgG with PMB was carried out by adding 10 mg of PMB to either 5 mg or 3 mg of IgG prepared in (a) at 4° C. overnight with gentle shaking followed by reduction with 0.1 mg/ml $NaBH_3CN$ in 20 mM $NaPO_4$ pH 6.5 for 3 hours at room temperature. The IgG-PMB was separated from the rest of the reaction products by gel filtration on a 10 ml P-10 column.

Figure 8:
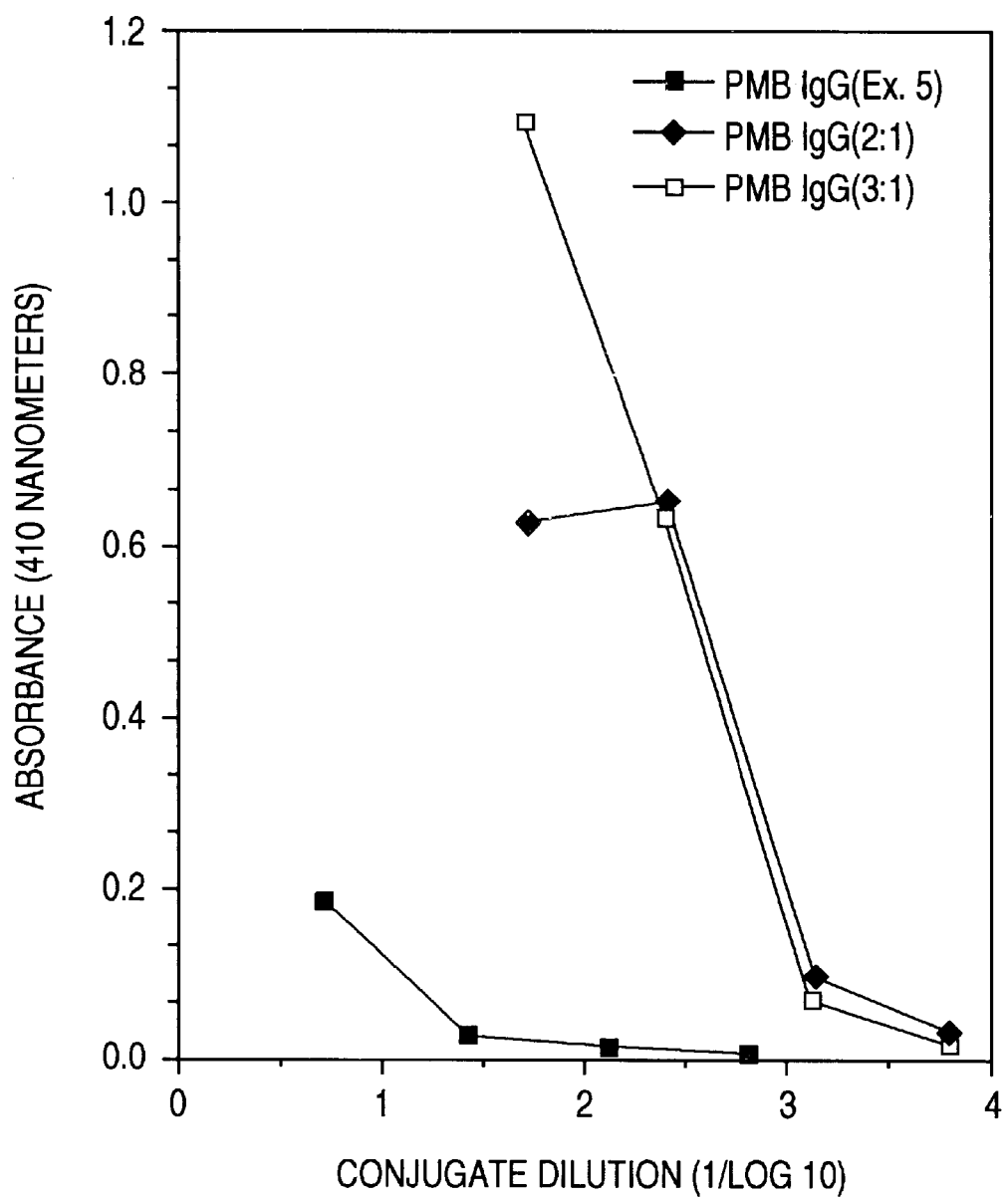
FIG. 8 shows periodate conjugates of the present invention binding to LPS, as measured by ELISA.

Inspection of the LPS binding activity (FIG. 8) revealed that the conjugates prepared were active. This is in contrast to the conjugate prepared in Example 5.

EXAMPLE 12

Antibacterial Activity of IgG-PMB Conjugates

Having determined which conjugates of IgG-PMB possessed LPS binding activity, the biological activity of the conjugates were examined (see discussion of Mode IV, above). Since polymyxin possesses direct antibiotic activity, it was possible that the conjugated polymyxin was also active. To determine whether the conjugates had any antibacterial activity, the minimum inhibitory concentration (MIC) and minimum bactericidal concentration MBC) for the SPDP conjugated IgG-PMB (107-fold molar excess of PMB, Example 8) and the periodate mediated IgG-PMB conjugate (3:1 ratio of PMB, Example 11) were determined. The example involved: (a) preparation of an *E. coli* bacterial inoculum; (b) determination of the MIC; and (c) determination of the MBC.

a) Preparation of an *E. coli* bacterial inoculum was initiated by first culturing *E. coli* HB101 strain overnight on TSA agar at 37° C. Colonies were suspended in sterile saline at $1.2 \times 10^8$ organisms/ml then diluted to $5 \times 10^5$ organisms/ml in Trypticase-Soy Broth (TSB; BBL). This concentration was confirmed by dilution plating.

b) Determination of MIC for each conjugate and a native polymyxin B control was made by mixing 0.5 ml of the $5 \times 10^5$ organisms/ml inoculum with 0.5 ml of a two-fold dilution series of each conjugate and incubating overnight in sterile 12×75 mm culture tubes at 37° C. The MIC was defined as the lowest concentration of the conjugate or PMB which resulted in complete inhibition of visible growth.

For the PMB control the MIC was found to be 0.031 μg/ml while for the SPDP conjugate the MIC was found to be 0.25 mg/ml. For the 3:1 (PMB:IgG) periodate conjugate the MIC was found to be 0.031 mg/ml which is approximately 1000-fold higher than for native PMB and eight-fold lower than for the SPDP IgG-PMB conjugate. Thus, both IgG-PMB conjugates do indeed retain antibacterial activity with the periodate conjugate exhibiting the highest degree of activity. The difference between the PMB and IgG-PMB values reflect in part the greater size of IgG (about 100 times that of PMB) in that if PMB activity was perfectly preserved during conjugation and one PMB molecule was conjugated to each IgG molecule, the MIC would increase 100-fold due to the size of the IgG. The 1000-fold shift observed suggests that the activity of PMB is reduced by conjugation and/or not all IgG molecules are conjugated. Nonetheless, it is surprising that a small surface-active antibiotic can still inhibit bacterial growth when conjugated to a much larger protein.

c) Determination of the MBC for each conjugate was made by plating serial dilutions of the mixtures in (b) above that exhibited no growth on TSA agar overnight at 37° C. The MBC was defined as the lowest concentration of conjugate on PMB which resulted in 99.9% of the viable organisms in the primary inoculum being killed. The MBC for the PMB was found to be 0.031 μg/ml, for the SPDP IgG-PMB to be 0.5 mg/ml, and for the periodate to be 0.031 mg/ml. The ability of the IgG-PMB conjugates to suppress bacterial growth and to kill bacteria on contact suggests that these compounds may be effective in preventing or treating bacteremia.

EXAMPLE 13

The Effect of IgG-PMB Conjugate on Complement and its Activation by LPS

Both immunoglobulin and LPS have the potential to interact with complement. The interaction of LPS with complement can exacerbate the inflammatory response to endotoxemia or bacteremia. In this example, the ability of IgG-PMB conjugate to block complement activation by LPS was investigated. In addition, since immunoglobulin can also trigger adverse complement reactions [S. Barandun et al., Vox Sang., 7:157–174 (1962)], the ability of conjugate alone to activate complement was also determined. The example involved: (a) determination of the LPS concentrations sufficient to activate complement; and (b) blocking LPS-induced complement activation with IgG-PMB.

a) Determination of the LPS concentrations sufficient to activate complement was carried out by adding varying concentrations of LPS to a standard quantity of a complement source CH50 (Reference Standard; Sigma) and measuring the amount of complement liberated by titration on sensitized sheep red blood cells (SRBCs) [modification of A. Chonn et al., J. Immunol., 146:4234–4241 (1991)].

To 40 μl of the Reference Standard, 40 μl of solution containing 80 μg, 8 μg, 0.8 μg, 0 μg of *E. coli* LPS or GVB+2 buffer (Sigma) were added, mixed, and incubated for 30 minutes at 37° C. Five or 10 μl aliquots of each mixture or a blank control were then added to CompQuick CH50 tubes (Sigma), mixed by repeated inversion and incubated for 60 minutes at room temperature with occasional mixing. The tubes were then centrifuged at 600×g for 10 minutes at 4° C. and the hemolysis present in the supernatant measured at 415 nm versus the lysis control blank solution. The $CH_{50}$ value of each mixture was calculated as follows:

$$CH_{50} \text{ of sample} = \frac{\text{absorbance sample}}{\text{absorbance standard}} \times CH_{50} \text{ of reference standard}$$

TABLE 17

Activation of Complement by LPS

| Sample Tested | Abs. @ 415 nm | $CH_{50}$ Value | % Decrease |
|---|---|---|---|
| 1.0 mg/ml LPS + Ref. Std. | 0.124 | 114.7 | 51.2 |
| 0.1 mg/ml LPS + Ref. Std. | 0.170 | 157.8 | 33.1 |
| 0.01 mg/ml LPS + Ref. Std. | 0.215 | 198.9 | 15.4 |
| Reference Standard | 0.254 | 235.0 | 0 |

These results show that preincubation of a complement source with LPS liberates complement which is then unavailable for action on SRBCs in the second phase of the assay. The LPS effect was concentration-dependent.

b) Blocking of LPS-induced complement activation with IgG-PMB was carried out by mixing SPDP-conjugated IgG-PMB prepared as described in Example 7 with LPS and then examining the effect of pretreated LPS on complement activation. To 1.5 μg of *E. coli* 026:B6 LPS, 7.5 μg of IgG PMB or 15 μl of a buffer control was added and incubated at 37° C. for 60 minutes. Thirty (30) μl of complement (Ref-Std as in (a) above) or GVB+2 buffer was added to each sample and incubated for 60 minutes at 37° C. Twenty (20) μl of each mixture was added to CompQuick CH50 tubes (Sigma), mixed and incubated for 60 minutes at room temperature. The tubes were centrifuged as in (a) above and hemolysis quantitated at 415 nm. The results are shown in Table 18.

TABLE 18

Inhibition of LPS-Mediated Complement Activation by IgG-PMB

| Sample Tested | Abs. @ 415 nm | $CH_{50}$ Value | % Δ |
|---|---|---|---|
| IgG-PMB only | 0.002 | 0.40 | — |
| IgG-PMB + Complement | 1.273 | 253.1 | +7.7 |
| LPS only | 0.008 | 1.59 | — |
| Complement | 1.182 | 235 | 0 |
| LPS + Complement | 0.806 | 160.2 | −31.8 |
| IgG-PMB + LPS + Complement | 1.237 | 245.9 | +4.6 |

The results show that preincubation of IgG-PMB with LPS blocks the effect of LPS on complement activation.

Furthermore, the IgG-PMB conjugate has no effect on complement activation on its own suggesting that cross-linking with PMB has not perturbed IgG structure such that it would have a deleterious effect through spontaneous complement reactions. The ability to block LPS effects and the apparent safety of the IgG-PMB conjugate suggests that it could possess both prophylactic and therapeutic value against bacteremia and endotoxemia.

EXAMPLE 14

Improved IgG-PMB Conjugates

Methods were investigated for improving the activity of the IgG-PMB conjugates prepared by the methods of Example 7 (SPDP) and Example 11 (periodate oxidation/Schiff base reduction). Since both families of conjugates exhibited much higher levels of LPS-binding than conjugates prepared with other chemistries, it was possible that even higher levels of binding could be achieved by increasing the degree of PMB-substitution on the IgG. The two mechanisms employed for achieving greater substitution were to increase the reactant (IgG and PMB) concentration at the conjugation step and to use more highly derivatized SPDP-PMB. The example involved: (a) preparation of a new periodate IgG-PMB conjugate; (b) preparation of new SPDP IgG-PMB conjugates; (c) ELISA of conjugate binding to LPS; (d) determination of conjugate MICs and MBCs; and (e) determination of the degree of conjugation by amino acid analysis.

a) Preparation of a new periodate IgG-PMB conjugate was carried out by oxidizing 30 mg of IgG dissolved in 1 ml of 50 mM $NaPO_4$ pH 7.2 with 10.7 mg of sodium periodate (Sigma) for 30 minutes at room temperature. The 1 ml reaction mixture was applied to a 15 ml Swift desalting column equilibrated in 50 mM $NaPO_4$ pH 7.2 and the peak IgG fractions were pooled to an IgG concentration of 7.1 mg/ml. To 1 ml of this Ig mixture containing 0.0476 μmoles of IgG, 20 mg of PMB (14.44 μmoles) was added and incubated overnight at 4° C. The pH of the reaction mixture was adjusted to pH 6.5 with 1.0 N HCl and 10 μl of a 10 mg/ml $NaBH_3CN$ solution was added and incubated at room temperature for 4 hours. The conjugate was then chromatographed on a 10 ml P-10 column and stored at 4° C.

b) Preparation of new SPDP IgG-PMB conjugates was carried out by first derivatizing PMB at a 2:1 and 3:1 molar ratio of SPDP:PMB as described in Example 6. For each reaction 5 mg of IgG in 0.5 ml was derivatized with 15 μl of 20 mM SPDP solution in DMSO by incubating for 30 minutes at room temperature with intermittent shaking. The derivatized IgG was purified on a 15 ml Swift desalting column equilibrated with acetate buffer and the peak fractions were pooled and concentrated on a Centriprep-30 concentrator (Amicon). To the 5 mg of IgG in 1.8 ml of acetate buffer, 7.7 mg of dithiothreitol in 250 μl of acetate buffer was added and incubated at room temperature for 30 minutes. Each sample was then purified on a 15 ml Swift desalting column equilibrated in PBS-EDTA. To each sample containing approximately 5 mg of SPDP derivatized IgG, 5 mg of PMB derivatized at either a 2:1 or 3:1 molar ratio of SPDP was added and incubated for 18 hours at room temperature. Each conjugate was then separated from free SPDP-PMB by gel filtration on a P-10 column (50 ml) equilibrated with PBS-EDTA and the peak fractions were collected, pooled, and stored at 4° C.

c) ELISA of conjugate binding to LPS was performed as described in Example 1 using E. coli 0111:B4 LPS (Sigma).

The binding of different dilutions of the periodate conjugate made in (a) above, and the two SPDP conjugates made in (b) above to LPS coated and uncoated wells of a 96 well microtiter plate are shown as averages of duplicate samples in Table 19.

TABLE 19

LPS-Binding Activity of New IgG-PMB Conjugates

| | | Abs 410 nm | |
|---|---|---|---|
| Conjugate Tested | Conjugate Dilution | w/Ag | w/o Ag |
| IgG-PMB (IO$_4$) | 1:10 (=0.1 mg/ml) | 1.788 | 1.694 |
| | 1:50 | 1.392 | 0.632 |
| | 1:250 | 0.440 | 0.096 |
| | 1:1250 | 0.121 | 0.039 |
| | 1:6250 | 0.035 | 0.009 |
| IgG-PMB (SPDP) 3:1 | 1:10 (=0.09 mg/ml) | 1.726 | 0.718 |
| | 1:50 | 1.650 | 0.156 |
| | 1:250 | 0.979 | 0.167 |
| | 1:1250 | 0.520 | 0.013 |
| | 1:6250 | 0.120 | 0.007 |
| IgG-PMB (SPDP) 2:1 | 1:10 (=0.1 mg/ml) | 1.592 | 0.375 |
| | 1:50 | 1.256 | 0.057 |
| | 1:250 | 0.578 | 0.015 |
| | 1:1250 | 0.151 | 0.008 |
| | 1:6250 | 0.028 | 0.010 |

The results shows that the 3:1 SPDP:PMB conjugate had the highest specific LPS binding activity, approximately 2–4 times the binding exhibited by the 2:1 SPDP:PMB conjugate and the periodate conjugate at concentrations of 0.8–4.0 μg/ml.

d) Determination of conjugate MICs and MBCs was carried out exactly as described in Example 10 using E. coli HB101 as the susceptible test strain. The results are shown in Table 20.

TABLE 20

MIC and MBC for the New IgG-PMB Conjugates

| Conjugate | MIC | MBC |
|---|---|---|
| Periodate IgG-PMB | 7.8 μg/ml | 7.8 μg/ml |
| 2:1 SPDP IgG-PMB | 250 μg/ml | 250 μg/ml |
| 3:1 SPDP IgG-PMB | 125 μg/ml | >125 μg/ml |
| PMB Control | 0.039 μg/ml | 0.039 μg/ml |

When compared with these determinations for the conjugates examined in Example 12, the new periodate conjugate is four times as potent and the 3:1 SPDP-PMB conjugate is twice as potent. Surprisingly, the periodate conjugate exhibits lower LPS-binding activity by ELISA but stronger antibacterial activity than the 3:1 SPDP-PMB conjugate. Perhaps the modification of PMB and IgG with SPDP improves the conjugation efficacy but decreases the antibiotic activity compared to the conjugation of native PMB to periodate-treated IgG.

e) Determination of the degree of conjugation by amino acid analysis was carried out by examining the amino acid composition of 2:1 SPDP Ig-PMB, 3:1 SPDP Ig-PMB, and the periodate Ig-PMG conjugates above compared with control samples of native human IgG and free polymyxin B. The novel amino acid diaminobutyric acid (DAB) which constitutes 6 of the 10 residues of PMB was the key component that was detected and quantitated.

Five samples in all were analyzed, including:
1. Free PMB (25 nmoles in 50 μl $H_2O$)
2. Periodate Ig-PMB (600 pmoles in 100 μl PBS)

3. SPDP 3:1 Ig-PMB (600 pmoles in 100 μl PBS)
4. SPDP 2:1 Ig-PMB (600 pmoles in 100 μl PBS)
5. Human IgG (600 pmoles in 100 μl PBS)

The samples were prepared by transferring each to a glass hydrolysis tube using three rinses of 100 μl of pure water and then concentrated to dryness in a vacuum centrifuge. 500 μl of distilled 6N HCl, 10 μl of 2-mercaptoethanol, and 10 μl of a 50% aqueous phenol solution were added to each of the sample tubes, which were then purged with nitrogen gas and capped. The samples were hydrolyzed by heating at 110° C. for 22 hours and then concentrated again to dryness. The PMB sample was suspended in 500 μl of 0.2 N sodium citrate buffer, pH 2.2 while the other four samples were suspended in 250 μl of this buffer. After thorough mixing, the sample solutions were passed through a 0.2 μm pore nylon membrane syringe filter.

20 μl of each filtered hydrolysate solution was analyzed using a Beckman Instruments 6300 Amino Acid Analyzer. The machine was equipped with a Beckman 10 cm cationic exchange HPLC column, a Beckman sodium buffer system, a 60 minute analysis methodology, and a Beckman ninhydrin reagent detection system with absorbance measured at the 570 nm and 440 nm wavelengths. The detector sensitivity was set at 1.0 AUFS for the PMB sample and 0.5 AUFS for the other four samples.

All data collection and peak integration was performed with a Gilson HPLC System Controller 712 v. 1.1 software package (Middleton, Wis.). Sample peak identification and amino acid concentrations were determined by comparison to analyses made at known concentrations of a 17 amino acid standard mixture (Beckman Standard, Lot #A108039) and (S)-(+) 2,4-Diaminobutyric acid dihydrochloride (Aldrich Chemical, Lot #07301CY). The results of the amino acid analysis are shown in Table 21.

TABLE 21

Amino acid composition of Ig-PMB conjugates

| Amino Acid | Letter Code | Human IgG | PMB | IgG – PMB $10_4$ | IgG – PMB 1:2 | IgG – PMB 1:3 |
|---|---|---|---|---|---|---|
| Asp | D | 111 | | 107 | 105 | 111 |
| Thr | S | 117 | 2 | 120 | 115 | 122 |
| Ser | S | 177 | | 188 | 208 | 176 |
| Glu | E | 133 | | 129 | 129 | 136 |
| Pro | P | 119 | | 105 | 120 | 123 |
| Gly | G | 95 | | 101 | 102 | 101 |
| Ala | A | 75 | | 75 | 78 | 80 |
| Val | V | 116 | | 112 | 107 | 112 |
| Met | M | 9 | | 8 | 9 | 9 |
| Ile | l | 26 | | 28 | 25 | 26 |
| Leu | L | 99 | 1 | 105 | 96 | 100 |
| Tyr | Y | 51 | | 53 | 51 | 51 |
| Phe | F | 42 | 1 | 47 | 44 | 45 |
| His | H | 24 | | 24 | 23 | 23 |
| Lys | K | 83 | | 87 | 79 | 82 |
| Arg | R | 41 | | 44 | 38 | 39 |
| DAB | | | 6 | 20 | 11 | 22 |
| TOTAL | | 1318 | 10 | 1353 | 1340 | 1358 |
| moles PMB/mole IgG | | | | 3.3 | 1.8 | 3.7 |

The values represent the estimated amino acid composition of each sample, determined by multiplying the percentage of each amino acid measured by the expected total number of amino acids (1320 for human IgG, for example). The moles PMB/mole IgG were calculated by dividing the number of unique DAB residues detected by 6 (the number of DAB residues/PMB).

The results show that the 3:1 SPDP conjugate possessed the highest degree of conjugation (avg. 3.7 PMB molecules per IgG molecule). This is consistent with this conjugate possessing the highest LPS-binding activity as measured by ELISA (see (b) above). The 3:1 SPDP conjugate contained, on average, twice the number of PMB molecules than that of the 2:1 SPDP conjugate, which would explain the two-fold greater activity of the 3:1 SPDP conjugate in the LPS-binding ELISA. The periodate Ig-PMB is also well conjugated and it exhibited the highest degree of antibacterial activity. It appears that the SPDP linkage affords the highest degree of LPS-binding activity while the periodate linkage provides greater antibacterial activity. This may reflect steric differences in the way PMB is attached to the IgG and/or the different effects of the two conjugation chemistries on PMB activity.

EXAMPLE 15

Figure 9:
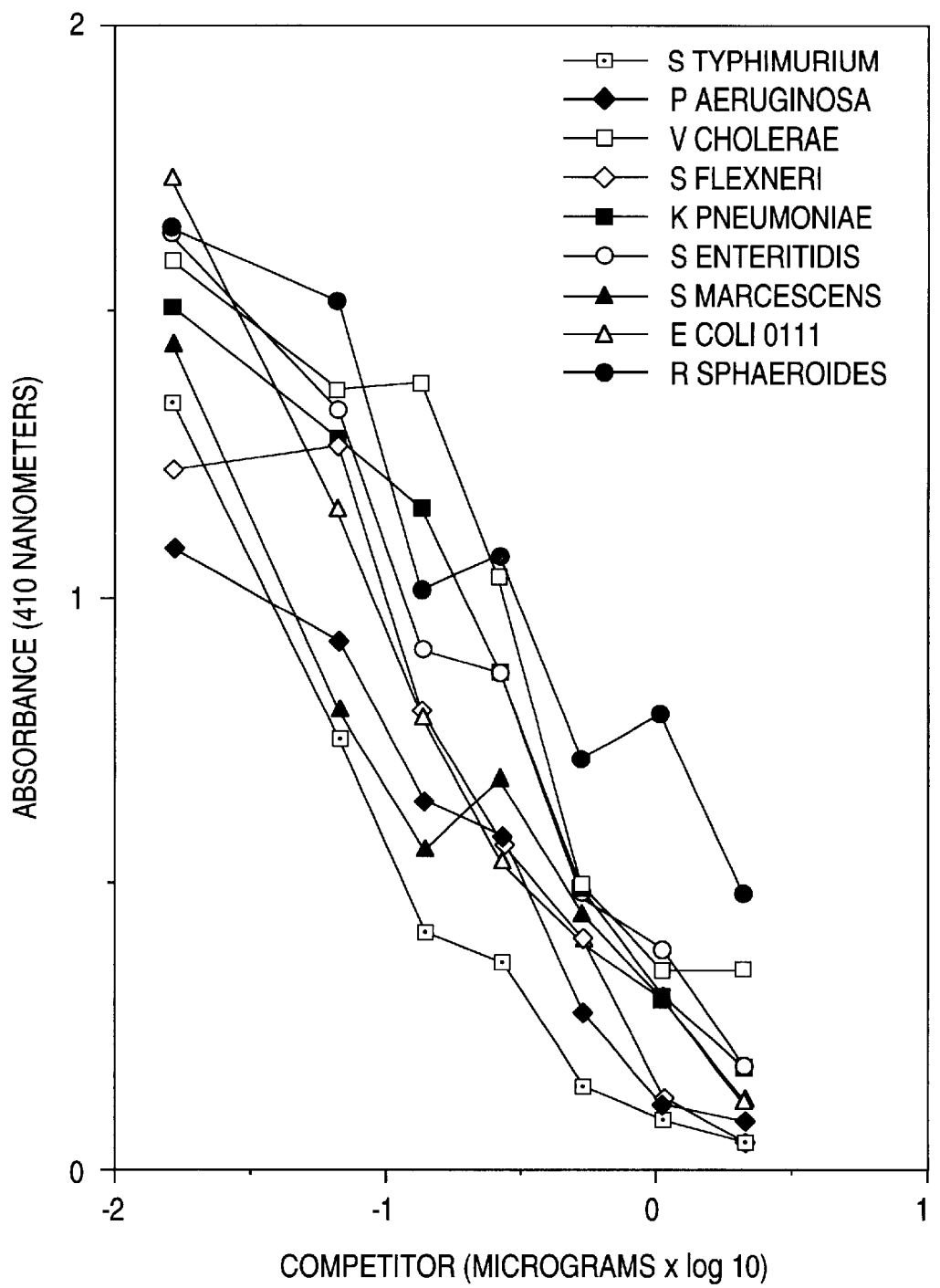
FIG. 9 shows inhibition of LPS binding of conjugates of the present invention using LPS of various bacterial species, as measured by ELISA.

The Use of IgG-PMB Conjugates as a Diagnostic: Cross-reactivity of Different Gram-Negative LPS Antigens with IgG-PMB Since the IgG-PMB conjugates exhibited binding to *E. coli* 0111:B4 LPS and this species is only one of many potential gram-negative agents of endotoxemia and bacteremia, it was of interest to determine whether the IgG-PMB conjugate was capable of detecting other species of LPS in a diagnostic format using a competitive ELISA. The example involved: (a) coating of *E. Coli* 0111:B4 LPS to microtiter wells; (b) incubation of IgG-PMB conjugates with different concentrations of several species of LPS; and (c) assay of conjugate binding to *E. coli* 0111:B4 LPS in the presence of competitor.

a) Coating of *E. coli* 0111:B4 LPS to the wells of 96-well microtiter ELISA plates was performed as described in Example 1 using 100 μl/well of pyrogen-free PBS containing 1 mM EDTA and 2 μg of LPS and coating overnight at 4° C. The wells were washed with PBS-0.05% Tween 20 and blocked with PBS containing 10 mg/ml endotoxin-free BSA at 37° C. for 90 minutes.

b) Incubation of IgG-PMB conjugates with different concentrations of LPS purified from *E. coli* 0111:B4 (control standard) *Salmonella typhimurium, Pseudomonas aeruginosa, Vibrio cholerae, Shigella flexneri, Klebsiella pneumoniae, Salmonella enteritiais, Serratia marcescens,* and *Rotobacter sphaeroides* (all from Sigma) was carried out by adding 250 μl of a 7.2 μg/ml solution of IgG-PMB conjugate prepared with a 3:1 molar ratio of SPDP:PMB (Example 13) to 250 μl of PBS-0.05% Tween 20 containing 1 mg/ml incubation at 37° C., 100 μl of these mixtures was added per well.

c) Assay of conjugate binding to *E. coli* 0111:B4 LPS in presence of competitor was measured by incubating 100 μl of the mixtures in (b) above at 37° C. for 1 hour. The plates were then washed and the wells incubated with alkaline phosphate-conjugated goat anti-human IgG (Sigma) diluted 1:500 in PBS 0.05% Tween 20 containing 1 mg/ml, incubated 37° C. for 1 hour, washed again and incubated in p-nitrophenyl phosphate for 30 minutes and read at 410 nm all as described in Example 1. The results are shown in FIG. 9 and demonstrate that LPS antigens from all nine species representing four different orders of gram-negative bacteria compete effectively for IgG-PMB binding to *E. coli* 0111:B4 LPS. These results show that IgG-PMB conjugates can be used to detect and quantitate a variety of LPS species and suggest that the IgG-PMB conjugate will be therapeutically effective against a broad spectrum of gram-negative organisms and endotoxins.

EXAMPLE 16

Neutralization of the In Vivo Effects of Endotoxin by IgG-PMB

Endotoxin (LPS) can trigger a lethal reaction in vivo. In order to determine whether IgG-PMB conjugate is capable of neutralizing the lethal effects of endotoxin, a murine model of endotoxic shock was utilized [C. Galanos et al., Proc. Natl. Acad. Sci. USA 76:5939–5943 (1979)]. The example involved: (a) determination of a minimum lethal dose of endotoxin in galactosamine-sensitized mice; and (b) neutralization of endotoxin lethality by premixture with Ig-PMB.

a) Determination of a minimum lethal dose of endotoxin in galactosamine-sensitized mice was performed by administering different doses of E. coli 0111:B4 LPS to C57Bl/6 mice that were co-administered 20 mg of D-galactosamine-HCl in 400 μl of PBS. The latter compound is a specific hepatotoxic agent that increases the sensitivity of experimental animal to endotoxin several thousand-fold [C. Galanos et al., Proc. Natl. Acad. Sci. USA 76:5939–5943 (1979)]. 1–500 ng of E. coli 0111:B4 LPS (List Biological Laboratories, Campbell, Calif.) was injected intraperitoneally in PBS along with 20 mg of D-galactosamine (Sigma). It was found that 10–25 ng of endotoxin was usually sufficient to kill most or all mice within 24 hr. The variability in endotoxin lethality may be related to the different ages of the mice used. Since 10 ng was the minimal effective lethal dose, this amount of LPS was utilized in neutralization experiments.

b) Neutralization of endotoxin lethality by premixture with Ig-PMB was performed by incubating 50 ng of E. coli 0111:B4 LPS with 5 mg of periodate conjugated IgG-PMB (prepared as described in example 14), or 5 mg of unconjugated control human IgG (Sigma) and 100 mg D-galactosamine in PBS and injecting a portion of each mixture intraperitoneally into C57BL/6 mice. The results are shown in Table 22. Survival was assessed 24 hours later.

TABLE 22

Neutralization of Endotoxin Lethality by IgG-PMB (Therapeutic Prophylactic)

| Treatment | #Survivors/Total |
|---|---|
| 1 mg human IgG and 20 mg D-galactosamine | 5/5 |
| 1 mg human IgG, 10 ng LPS, and 20 mg D-galactosamine | 1/4 |
| 1 mg periodate IgG-PMB, 10 ng LPS, and 20 mg D-galactosamine | 5/5 |

Since the number of animals used in this experiment was small, the trial was repeated using a) 12 mice in the control group treated with endotoxin, D-galactosamine, and normal human IgG and b) 12 mice in the experimental group that received endotoxin, D-galactosamine, and the periodate IgG-PMB. The per mouse dosage of each component was the same as above and the experiment was repeated exactly as above. The results are shown in Table 23.

TABLE 23

Neutralization of Endotoxin Lethality by IgG-PMB

| Treatment | Survivors/Total |
|---|---|
| 1 mg human IgG, 10 ng LPS, and 20 mg D-galactosamine | 0/12 |
| 1 mg periodate IgG-PMB, 10 ng LPS, and 20 mg D-galactosamine | 11/12 |

The results of the two trials prove that IgG-PMB neutralizes the lethal effect of endotoxin in vivo and suggest that Ig-PMB conjugates will be useful in preventing or treating sepsis due to gram-negative bacteria.

EXAMPLE 17

Prevention of Endotoxin Lethality by Prophylactic Administration of IgG-PMB Conjugate In the previous example, the ability of IgG-PMB conjugate to neutralize endotoxin lethality in vivo was investigated by mixing conjugate or control IgG with endotoxin and administering the mixture with D-galactosamine into mice. The results showed that the conjugate neutralized the endotoxin. A more strenuous test of the ability of the conjugate to neutralize endotoxin lethality is to administer the conjugate at a separate time and via a separate route than the endotoxin. In addition, to demonstrate its prophylactic value, lower doses of conjugate were utilized. The example involved the intravenous administration of IgG-PMB or control IgG followed 1 hr later by the intraperitoneal administration of a lethal dose of endotoxin and D-galactosamine.

Twenty (20) CS7BL/6 mice weighing twenty (20) grams each were administered 200 μg (5 mice) or 400 μg (8 mice) of IgG-PMB conjugate (periodate conjugate prepared as in Example 14) or 400 μg control human IgG (7 mice) in 100 μl of PBS through their tail vein. Ninety (90) minutes later, each mouse received 10 ng E. coli 0111:B4 endotoxin and 20 mg D-galactosamine in 200 μl of PBS administered intraperitoneally. After 24 hrs, the number of mice surviving in each group was recorded. The results are shown in Table 24.

TABLE 24

Prophylaxis Against Endotoxin in Challenge With IgG-PMB Conjugate

| Treatment | # Survivors/Total |
|---|---|
| 400 μg human IgG; 10 ng endotoxin and 20 mg D-galactosamine | 0/7 |
| 200 μg IgG-PMB; 10 ng endotoxin and 20 mg D-galactosamine | 5/5 |
| 400 μg IgG-PMB; 10 ng endotoxin and 20 mg D-galactosamine | 8/8 |

The results show that a 10–20 mg/kg dose of IgG-PMB administered intravenously is sufficient to protect against a subsequent lethal challenge of endotoxin administered intraperitoneally. These findings suggest that the IgG-PMB conjugate given prophylactically will prevent endotoxin-mediated effects and that the conjugate is capable of neutralizing endotoxin outside of the vascular compartment.

EXAMPLE 18

Preservation of IgG Effector Functions in IgG-PMB Conjugates: Fc Receptor Binding One of the functions of IgG is to opsonize and facilitate clearance of organisms, toxins, antigens, etc. by phagocytic cells. In order to determine whether this property of IgG, which is facilitated by the Fc region of the native molecule, remains intact in IgG conjugates that have been prepared with SPDP or periodate, the binding of IgG-PMB to human monocyte/macrophage cells was examined in a competition assay. This assay is similar to that employed to examine the Fc receptor binding activity of hybrid recombinant antibody fragments fused to cell surface viral receptors [D. J. Capon et al., Nature 337:525–531 (1989); A. Traunecker et al., Nature 339:68–70 (1989)]. The example involved: (a) preparation of a control conjugate of PMB to human albumin (a non-Fc receptor binding human protein-PMB conjugate); and (b) assay of IgG-PMB conjugate binding to Fc receptors of the human U937 monocyte/macrophage cell line.

a) In order to compare the specific properties of IgG-PMB conjugates with other protein-PMB conjugates, human albumin was conjugated with PMB using the SPDP chemistry of Example 7 (because albumin is not glycosylated, the periodate chemistry of Example 5 was not applicable to albumin). Conjugation of albumin with PMB was carried out in three steps similar to the scheme described in Example 7. The first step involved derivatization of 10 mg of PMB in 50 mM sodium borate, 300 mM NaCl pH 9.0 with 2:1 mg of SPDP dissolved in 50 µl of dimethylsulfoxide for 30 minutes at room temperature. The free cross-linker was removed on a 15 ml Swift desalting column as described in Example 7.

Ten (10) mg of human serum albumin was derivatized with 1.2 mg of SPDP (in 25 µl DMSO) dissolved in 1 ml of 50 mM sodium borate, 300 mM NaCl pH 9.0 and mixed for 30 minutes at room temperature. The free cross-linker was removed by gel filtration on a 15 ml Swift desalting column equilibrated with PBS-EDTA pH 7.5 and the peak fractions containing SPDP-albumin were collected pooled and concentrated on a Centriprep-30 concentrator. The pH of the sample was raised to 8.0 with 10 µl 10N NaOH and reduced with 15.4 mg dithiothreitol dissolved in 200 µl of pyrogen-free water for 30 minutes at room temperature. The reduced, derivatized albumin was purified by gel filtration on a 15 ml desalting column and concentrated on a Centriprep-30 concentrator.

The reduced, derivatized albumin was conjugated with SPDP-PMB by mixing the two solutions prepared above and incubating overnight at room temperature. The conjugate was separated from SPDP-PMB by gel filtration on a 50 ml P-10 column.

b) Assay of IgG-PMB conjugate binding to Fc receptors of the human U937 monocyte/macrophage cell line was performed in a manner similar to that described by Capon et al. [Nature 337:525–531 (1989)]. First, a saturation curve of the binding of $^{125}$I-labelled human IgG [the $^{125}$I-IgG stock concentration was 16 µg/ml =1.07×10$^{-7}$ M] (New England Nuclear, Boston, Mass.) was performed by incubating $1\times10^{-8}$ M–$1\times10^{-12}$ M $^{125}$I-IgG with $2\times10^5$ U937 cells in 0.5 ml of PBS containing 2 mg/ml BSA and 0.1% sodium azide. The cell suspensions were incubated for 60 minutes at 37° C., centrifuged for 3 minutes at 1500 xg and washed three times with incubation buffer. The cell pellets were then counted for radioactivity with a Bioscan "Quick Count" benchtop radioisotope counter (Bioscan, Inc., Washington D.C.). The binding was found to saturate at $1\times10^{-8}$ M $^{125}$I-Ig so this concentration was used for the competition assay below.

Figure 10:
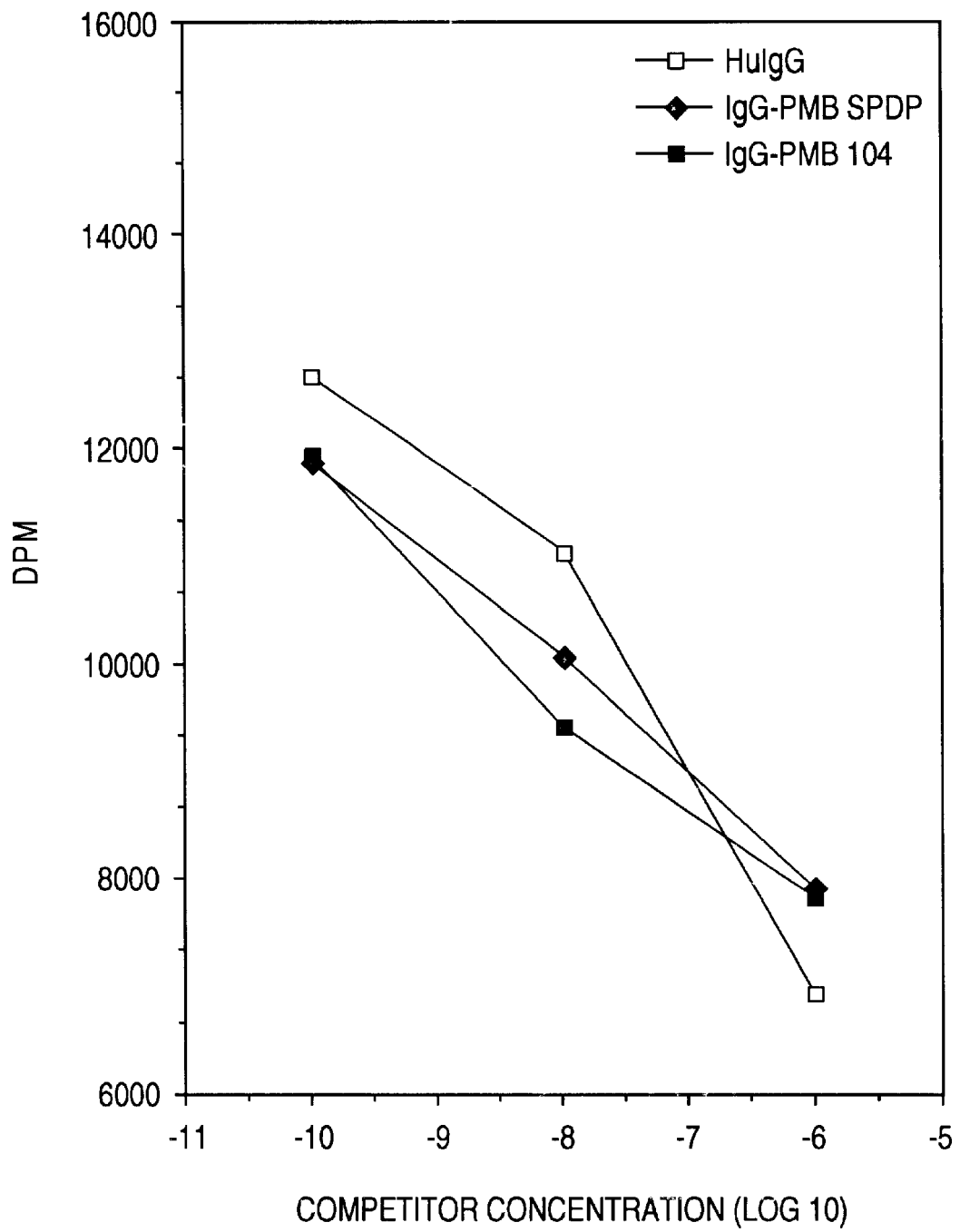
FIG. 10 shows the binding of conjugates of the present invention to phagocytic cells in a radioactive competition assay.

For the competition experiment, a constant quantity of $^{125}$I-IgG ($1\times10^8$ M) was incubated with $2\times10^5$ U937 cells in 0.5 ml of PBS containing 2 mg/ml BSA, 0–1% sodium azide and varying concentrations of the unlabelled competitor proteins: human IgG, IgG-PMB (SPDP), IgG-PMB (periodate), and human albumin-PMB from (a) above. The cells were incubated, washed, and radioactive $^{125}$I-IgG bound quantitated as described above. In the absence of any of the human competitor proteins, 12,029 dpm was bound to the cells. The results of the competitor assay are plotted in FIG. 10. It is clear that human IgG and both IgG-PMB conjugates have similar binding properties to the U937 cells in that all three compete comparably well at $10^{-8}$ M and $10^{-6}$ M. This result shows that the modification of the IgG with SPDP and PMB or by periodate oxidation of the carbohydrate side chains does not impair the ability of IgG to bind to Fc receptors. This suggests that the conjugates can facilitate Fc receptor mediated opsonization of antigen/organisms by phagocytic cells. As expected, the human albumin-PMB exhibited no competitive binding activity at concentrations up to $10^{-6}$ (data not shown) and is therefore unable to facilitate opsonization.

EXAMPLE 19

Preparation of an Antibody-Antibiotic Conjugate with Activity Against Gram-Positive Bacteria: IgG-Bacitracin Gram-positive organisms are responsible for approximately one-third of sepsis cases. It would be desirable to have IgG-antibiotic conjugates with activity against these organisms. To this end, conjugates were made between IgG and bacitracin and vancomycin, two surface-active gram-positive antibiotics. The example involved: (a) periodate activation of IgG; and (b) conjugation to bacitracin and vancomycin.

a) Periodate activation of IgG was carried out as described in Example 5(b) using 30 mg of human IgG and 50 mM sodium periodate in 1 ml of 50 mM NaPO$_4$ pH 7.2 for 30 minutes at room temperature. The activated IgG was purified on a 15 ml Swift desalting column (Pierce) and the peak fractions pooled.

b) Conjugation to bacitracin and vancomycin was carried out by adding 18.6 mg of bacitracin to 7.1 mg of activated IgG and 19.7 mg of vancomycin to 7.1 mg of activated IgG and each solution was incubated overnight at 4° C. After the reactions, the mixtures were clarified by centrifugation to remove precipitate that had formed. The reaction mixtures were adjusted to pH 6.5 with 1.0 N HCl and 10 µl of a NaCNBH$_3$ solution (10 mg/ml) was added and incubated for 4 hours at room temperature. The conjugate was then purified on a 15 ml Swift desalting column equilibrated in PBS-EDTA, pH 7.2.

EXAMPLE 20

Antibacterial Activity of IgG-Antibiotic Conjugate on Gram-Positive Bacteria

To determine if the conjugates prepared in Example 16 possessed anti-bacterial activity, the MIC and MBC of these conjugates was assayed against *Staphylococcus epidermidis* obtained from Dr. Edward Balish, Department of Medical Microbiology, University of Wisconsin. The strain is gram-positive, DNase negative, manitol salt negative, coagulase negative and novobiocin sensitive. The example involved:

(a) preparation of an *S. epidermidis* inoculum; and
(b) determination of the MIC and MBC of free and conjugated antibiotics.

a) Preparation of an *S. epidermidis* inoculum was carried out by plating organisms on TSA agar overnight at 37° C. and suspending bacteria at $5\times10^5$ organisms/ml in TSB.

b) Determination of the MIC and MBC of the free and conjugated antibiotics was carried out by mixing 0.5 ml of the S. epidermidis inoculum with 0.5 ml of solutions containing 0.3125–10 µg/ml of free antibiotic or 12.5–250 µg/ml of each conjugate. The MIC was defined as the minimum concentration of the compounds that inhibited visible growth and the MBC defined as the concentration that killed 99.9% of the initial organisms present in the inoculum (measured by plating those solutions that do not exhibit visible growth; see Example 10). The results are shown in Table 25.

TABLE 25

MIC and MBC of Free and IgG-Conjugated Antibiotics on S. epidermidis

| Compound | MIC(µg/ml) | MBC (µg/ml) |
| --- | --- | --- |
| Bacitracin | 25 | 50 |
| IgG-Bacitracin | 125 | 250 |
| Vancomycin | 1.25 | 2.5 |
| IgG-Vanomycin | >50 | N.D. |

The results show that the IgG bacitracin conjugate was indeed active against S. epidermidis and suggest that this compound could be useful in the prevention and treatment of gram-positive sepsis.

EXAMPLE 21

Treatment of Persons Susceptible to Gram-Negative Sepsis and Endotoxemia with an Antibody-Antibiotic Conjugate As noted earlier, studies have suggested a causal relationship between a person's humoral immune status and the susceptibility to gram-negative infections. The present invention contemplates screening for patients having a poor immune status for determining a subpopulation having the greatest need for antibodiotics. The example involves: (a) assay of patient total IgG and IgM levels; (b) assay of patient endotoxin core antigen-specific IgG and IgM levels; (c) comparison of patient immunoglobulin levels to healthy normal controls; (d) administration of immunoglobulin and/or immunoglobulin-antibiotic conjugate to patients with significant deficiencies in total or core antigen-specific immunoglobulin levels.

(a) Assay of patient total IgG and IgM levels is performed by nephelometry using the Beckman Automated immunochemistry system (Beckman Instruments, Inc., Brea, Calif.) as described by Stoll et al., Serodiagnosis and Immunotherapy 1:21–31 (1987).

(b) Assay of endotoxin in core-antigen specific IgG and IgM levels is performed by ELISA. Plasma or sera are diluted and the level of binding of different sample dilutions to purified E. coli J5 endotoxin and Salmonella minnesota R595 endotoxin are quantitated and compared with known standards of purified anti-endotoxin antibodies [B. J. Stoll et al., Serodiagnosis and Immunotherapy 1:21–31 (1987); M. Pollack et al., J. Clin. Invest., 72:1874–1881 (1983)].

c) Comparison of patient immunoglobulin levels to healthy controls is performed by analyzing the total IgG and IgM levels (as mg/ml of sample) in the patient vs. the control group and the endotoxin core antigen-specific IgG and IgM levels (as µg/ml of sample) between these same two groups. Patients with ≦80% of the normal control level of total IgG and/or ≦60% of the normal control level of endotoxin core antigen-specific IgG and IgM are defined as at risk for gram-negative infection and endotoxemia.

d) Administration of immunoglobulin and/or immunoglobulin antibiotic conjugate to patients with significant deficiencies in total or core antigen-specific immunoglobulin levels is carried out to restore normal or near normal total and antigen-specific humoral defenses. To restore normal IgG levels, a 3% solution of intravenously injectable immunoglobulin (available from Sandoz Forschungsinstitut, Vienna, Austria; Hyland Therapeutics, Duarte, Calif.; or Cutter Laboratories, Berkeley, Calif.) is administered twice daily until immunoglobulin levels rise to within 10% of normal levels.

Because the IgG-PMB conjugates of the present invention comprise a population of antibody molecules all of which are capable of binding to endotoxin, much less IgG-PMB conjugate is required than total IgG to restore or increase levels antigen-specific antibody. A single intravenous dose consisting of 1–20 mg of IgG-PMB conjugate per kg of body weight is administered to restore endotoxin-specific antibody levels to ≧100% of normal levels.

EXAMPLE 22

Treatment of Persons Susceptible to Gram-Negative Sepsis, Endotoxemia, and Gram-Positive Sepsis with a Cocktail of Antibody-Antibiotic Conjugates Since there is a casual relationship between a person's humoral status and their susceptibility to infections, there is also a need to restore antibody levels against gram-positive organisms as well as the levels against gram-negative organisms and endotoxin. This is achieved by administration of a cocktail of antibody-antibiotic conjugates with activity against both classes of bacteria as well as endotoxin. The example involves: (a) identification of persons at risk of infection; and (b) administration of a cocktail of antibody-antibiotic conjugates and, if necessary, total pooled human immunoglobulin to restore antigen-specific and total immunoglobulin levels.

a) Identification of persons at risk of infection is carried out by the means defined in Example 21.

b) Administration of a cocktail of antibody-antibiotic conjugates and, if necessary, total pooled human immunoglobulin to restore antigen-specific and total immunoglobulin levels is carried out by injecting a single intravenous dose of IgG-PMB (1–20 mg/kg) and a single intravenous dose of IgG-bacitracin conjugate (1–20 mg/kg) to increase the levels of gram-negative and gram-positive-reactive antibodies, respectively. If total immunoglobulin levels are also ≦80% of normal, a 3% solution of intravenously injectable immunoglobulin (available from Sandoz Forschunginstitut, Vienna, Austria; Hyland Therapeutics, Duarte, Calif.; or Letter Laboratories, Berkeley, Calif.) is administered twice daily until immunoglobulin levels rise to within 10% of normal levels.

What is claimed is:

1. An antibiotic-antibody conjugate, comprising surface-active antibiotic covalently bound via a non-carbodiimide cross-linker to non-specific immunoglobulin having an Fc region wherein said conjugate binds to bacteria via said antibiotic.

2. The conjugate of claim 1, wherein said immunoglobulin is IgG.

3. The conjugate of claim 2, wherein said IgG binds to phagocytic cells via said Fc region.

4. The conjugate of claim 1, wherein said conjugate is bacteriostatic.

5. The conjugate of claim 1, wherein said conjugate is bactericidal.

6. The conjugate of claim 1, wherein said bacteria are gram positive bacteria.

7. The conjugate of claim 1, wherein said bacteria are gram negative bacteria.

8. The conjugate of claim 7, wherein said conjugate binds lipopolysaccharide on said gram negative bacteria.

9. The conjugate of claim 7, wherein said conjugate also binds free endotoxin.

10. The conjugate of claim 9, wherein said conjugate neutralizes free endotoxin.

11. The conjugate of claim 10, wherein said antibiotic is a polymyxin.

12. The conjugate of claim 11, wherein said polymyxin is polymyxin B.

13. An antibiotic-antibody conjugate, comprising an endotoxin-binding compound covalently bound via a cross-linker to non-specific immunoglobulin having an Fc region.

14. The conjugate of claim 13, wherein said immunoglobulin is IgG.

15. The conjugate of claim 14, wherein said IgG binds to phagocytic cells via said Fc region.

16. The conjugate of claim 13, wherein said conjugate binds to gram negative bacteria.

17. The conjugate of claim 16, wherein said conjugate is bacteriostatic.

18. The conjugate of claim 16, wherein said conjugate is bactericidal.

19. The conjugate of claim 13, wherein said endotoxin-binding compound is a polymyxin.

20. The conjugate of claim 19, wherein said polymyxin conjugate binds free endotoxin.

21. A therapeutic preparation, comprising surface-active antibiotic covalently bound via a cross-linking spacer to non-specific immunoglobulin G, wherein said preparation is bactericidal for both gram-positive and gram-negative organisms, and wherein said preparation after administration demonstrates a circulating serum half-life greater than twenty days.

22. The therapeutic preparation of claim 21, wherein said antibiotic is selected from the group consisting of cephalosporins and penicillins.

23. The therapeutic preparation of claim 21, wherein said surface-active antibiotic covalently bound to non-specific immunoglobulin comprises:

i) a first conjugate consisting of a first antibiotic covalently bound to non-specific immunoglobulin G; and ii) a second conjugate consisting of a second antibiotic covalently bound to non-specific immunoglobulin G.

24. The therapeutic preparation of claim 23, wherein said first antibiotic is polymyxin and said second antibiotic is bacitracin.

25. The therapeutic preparation of claim 21, wherein two different antibiotics are covalently bound to the same immunoglobulin molecule.

26. The therapeutic preparation of claim 25, wherein one of said antibiotics binds to gram-positive organisms and the other of said antibiotics binds to gram-negative organisms.

27. A method of treatment, comprising:

a) providing a mammal for treatment;

b) providing a therapeutic preparation, comprising a surface-active antibiotic covalently bound via a non-carbodiimide crosslinker to non-specific immunoglobulin; and c) administering said preparation to said mammal, prior to any symptoms of bacterial infection.

28. The method of claim 27, wherein said surface-active antibiotic is a polymyxin.

29. The method of claim 27, wherein said immunoglobulin is IgG.

30. The method of claim 27, wherein said administering is intravenous.

31. A therapeutic preparation comprising a mixture of: i) a first conjugate comprising a first antibiotic covalently bound to non-specific immunoglobulin G; and ii) a second conjugate comprising a second antibiotic covalently bound to non-specific immunoglobulin G, wherein said preparation after administration demonstrates a circulating serum half-life greater than twenty days.

32. The therapeutic preparation of claim 31, wherein one of said antibiotics binds to gram-positive organisms and the other of said antibiotics binds to gram-negative organisms.

* * * * *